(12) United States Patent
Christensen et al.

(10) Patent No.: US 12,102,499 B2
(45) Date of Patent: Oct. 1, 2024

(54) TWO-PART DENTAL SEALANT, METHOD OF APPLYING WITH A SYRINGE DEVICE, AND KIT

(71) Applicant: 3M INNOVATIVE PROPERTIES COMPANY, St. Paul, MN (US)

(72) Inventors: Randilynn B. Christensen, Pine Springs, MN (US); Kenton D. Budd, Woodbury, MN (US); Afshin Falsafi, Woodbury, MN (US); Mahmut Aksit, Woodbury, MN (US); Jana Ninkovic, St. Paul, MN (US); Jie J. Liu, Cottage Grove, MN (US); Mark B. Agre, Rochester, MN (US); Masayuki Nakamura, Woodbury, MN (US); Jason W. Bjork, Cottage Grove, MN (US); Bradley D. Craig, Lake Elmo, MN (US); Richard P. Rusin, Woodbury, MN (US); Paul J. Homnick, Lake Elmo, MN (US); Joel D. Oxman, Minneapolis, MN (US); Yizhong Wang, Woodbury, MN (US); Paul R. Klaiber, Mahtomedi, MN (US); Bill H. Dodge, Finlayson, MN (US)

(73) Assignee: Solventum Intellectual Properties Company, Maplewood, MN (US)

( * ) Notice: Subject to any disclaimer, the term of this patent is extended or adjusted under 35 U.S.C. 154(b) by 870 days.

(21) Appl. No.: 17/247,244

(22) PCT Filed: Jun. 4, 2019

(86) PCT No.: PCT/IB2019/054644
§ 371 (c)(1),
(2) Date: Dec. 4, 2020

(87) PCT Pub. No.: WO2019/234633
PCT Pub. Date: Dec. 12, 2019

(65) Prior Publication Data
US 2023/0134622 A1    May 4, 2023

Related U.S. Application Data

(60) Provisional application No. 62/681,567, filed on Jun. 6, 2018.

(51) Int. Cl.
*A61C 5/64* (2017.01)
*A61K 6/61* (2020.01)
(Continued)

(52) U.S. Cl.
CPC .................. *A61C 5/64* (2017.02); *A61K 6/61* (2020.01); *A61K 6/62* (2020.01); *A61K 6/79* (2020.01); *A61K 6/887* (2020.01)

(58) Field of Classification Search
CPC ....................................... A61K 6/887
See application file for complete search history.

(56) References Cited

U.S. PATENT DOCUMENTS 3,066,112 A    11/1962    Bowen
3,729,313 A    4/1973    Smith
(Continued)

FOREIGN PATENT DOCUMENTS

CN    101410022    4/2009
CN    107200184    9/2017
(Continued)

OTHER PUBLICATIONS

A Guide to Silane Solutions—Mineral and Filler Treatment, Dow Corning Corporation, 2009, 3 pages.
(Continued)

*Primary Examiner* — Michael F Pepitone

(57) ABSTRACT

A method of applying a two-part dental sealant is described comprising providing a syringe device (1) comprising a
(Continued)

cartridge (10) including first and second chamber. The first chamber contains a first part of a dental sealant comprising a (meth)acrylate resin and an oxidizing curing agent. The second chamber contains a second part of a dental sealant comprising a (meth)acrylate resin and a reducing curing agent that reacts with the oxidizing curing agent of the first chamber. The first and/or second part of the dental sealant further comprise a single component or multiple components that neutralize acid and promote remineralization. The syringe device comprises a dispensing nozzle (17) comprising a static mixer and an outlet at one end of the cartridge and a plunger (20) at the opposing end of the cartridge. Also described is a kit for storing and applying the dental sealant is described.

20 Claims, 3 Drawing Sheets

(51) Int. Cl.
    *A61K 6/62*     (2020.01)
    *A61K 6/79*     (2020.01)
    *A61K 6/887*    (2020.01)

(56) References Cited

U.S. PATENT DOCUMENTS

| | | | |
|---|---|---|---|
| 4,150,012 | A | 4/1979 | Joos |
| 4,209,434 | A | 6/1980 | Wilson |
| 4,503,169 | A | 3/1985 | Randklev |
| 4,632,672 | A | 12/1986 | Kvitrud |
| 4,871,786 | A | 10/1989 | Aasen |
| 5,100,320 | A | 3/1992 | Martin |
| 5,130,347 | A | 7/1992 | Mitra |
| 5,149,368 | A | 9/1992 | Liu |
| 5,154,762 | A | 10/1992 | Mitra |
| 5,156,885 | A | 10/1992 | Budd |
| 5,332,429 | A | 7/1994 | Mitra |
| 5,545,676 | A | 8/1996 | Palazzotto |
| 5,848,894 | A | 12/1998 | Rogers |
| 6,030,606 | A | 2/2000 | Holmes |
| 6,387,981 | B1 | 5/2002 | Zhang |
| 6,444,725 | B1 | 9/2002 | Trom |
| 6,444,726 | B1 | 9/2002 | Brunt |
| 6,572,693 | B1 | 6/2003 | Wu |
| 6,613,383 | B1 | 9/2003 | George |
| 6,685,966 | B1 | 2/2004 | Dominique |
| 6,730,156 | B1 | 5/2004 | Windisch |
| 7,036,944 | B2 | 5/2006 | Budd |
| 7,090,721 | B2 | 8/2006 | Craig |
| 7,090,722 | B2 | 8/2006 | Budd |
| 7,156,911 | B2 | 1/2007 | Kangas |
| 7,241,437 | B2 | 7/2007 | Davidson |
| 7,396,862 | B2 | 7/2008 | Weimer |
| 7,649,029 | B2 | 1/2010 | Kolb |
| 8,236,871 | B2 | 8/2012 | Hecht |
| 8,414,930 | B2 | 4/2013 | Liu |
| 8,449,904 | B1 | 5/2013 | Jung |
| 8,455,554 | B2 | 6/2013 | Kessler |
| 8,647,510 | B2 | 2/2014 | Kolb |
| 8,722,759 | B2 | 5/2014 | Craig |
| 9,193,849 | B2 | 11/2015 | Stelzig |
| 9,427,290 | B2 | 8/2016 | Boehm |
| 2003/0195273 | A1 | 10/2003 | Mitra |
| 2004/0224087 | A1 | 11/2004 | Weimer |
| 2005/0252413 | A1 | 11/2005 | Kangas |
| 2006/0051427 | A1 | 3/2006 | Talton |
| 2007/0183984 | A1 | 8/2007 | Haas |
| 2008/0058442 | A1 | 3/2008 | Hermansson |
| 2008/0152598 | A1 | 6/2008 | Basic |
| 2010/0272764 | A1 | 10/2010 | Latta |
| 2011/0213036 | A1 | 9/2011 | Park |
| 2012/0295214 | A1 | 11/2012 | Wang |
| 2015/0272834 | A1 | 10/2015 | Sun |
| 2015/0291778 | A1 | 10/2015 | Musick |
| 2016/0270879 | A1 | 9/2016 | Boehm |
| 2017/0063829 | A1 | 3/2017 | Raounak |
| 2017/0216152 | A1 | 8/2017 | Hecht |

FOREIGN PATENT DOCUMENTS

| | | |
|---|---|---|
| EP | 3 515 986 B1 | 3/2022 |
| GB | 1534261 | 11/1978 |
| JP | H03-267067 | 11/1991 |
| RU | 2429814 | 9/2011 |
| WO | WO 1997-035916 | 10/1997 |
| WO | WO 2001-030304 | 5/2001 |
| WO | WO 2001-030305 | 5/2001 |
| WO | WO 2001-030307 | 5/2001 |
| WO | WO 2003-063804 | 8/2003 |
| WO | WO 2005-039508 | 5/2005 |
| WO | WO 2005/117805 A1 | 12/2005 |
| WO | WO 2009/018464 A2 | 2/2009 |
| WO | WO 2015-187490 | 12/2015 |
| WO | WO 2016-005822 | 1/2016 |
| WO | WO 2016-205181 | 12/2016 |
| WO | WO 2017-180545 | 10/2017 |
| WO | WO 2018-057503 | 3/2018 |
| WO | WO 2018-102484 | 6/2018 |
| WO | WO 2019-234661 | 12/2019 |

OTHER PUBLICATIONS

Adamson, "S 32. Aminoalkyl Tertiary Carbinols and Derived Products. Part I. 3-Amino-1: 1-Diphenylpropan-1-ols", Journal of the Chemical Society, 1949, Part 1, pp. S144-S155.
Ana, "Effects of Added Bioactive Glass on the Setting and Mechanical Properties of Resin-Modified Glass Ionomer Cement", Biomaterials, Aug. 2003, vol. 24, No. 18, pp. 3061-3067.
Arkles, "Silane Coupling Agents: Connecting Across Boundaries," v2.0, Gelest Inc., 2006, 12 pages.
Baechle, "Fluidized Bed Sputtering for Particle and Powder Metallization", Army Research Laboratory, Apr. 2013, ARL-TR-6435, pp. 1-34.
Hirano, "Treatment of Inorganic Filler Surface by Silane-Coupling Agent: Investigation of Treatment Condition and Analysis of Bonding State of Reacted Agent", International Journal of Chemical, Molecular, Nuclear, Materials and Metallurgical Engineering, Jan. 2012, vol. 6, No. 1, pp. 1-5.
Mishra, Handbook of Encapsulation and Controlled Release (2015), 329-344.
Nasanova, "Multifunctional Particle Coating by Plasma Process and Its Application to Pollution Control", RSC Advances, Jun. 2014, vol. 4, No. 56, pp. 29866-29876.
Sarkar, "A Modified Portland Cement for Dental Use: Its Interaction with Simulated Oral Environment", Transactions of the Indian Ceramic Society, Nov. 2014, vol. 4, No. 56, pp. 200-204.
Sulzer, "MIXPAC™ the Diversity of our Dental Applications", 24 pages.
International Search Report for PCT International Application No. PCT/US2017/063829, mailed on Mar. 15, 2018, 5 pages.
International Search Report for PCT International Application No. PCT/IB2019/054644, mailed on Sep. 17, 2019, 6 pages.
International Search Report for PCT International Application No. PCT/IB2019/054690, mailed on Oct. 21, 2019, 5 pages.

TWO-PART DENTAL SEALANT, METHOD OF APPLYING WITH A SYRINGE DEVICE, AND KIT

CROSS REFERENCE TO RELATED APPLICATIONS

This application is a national stage filing under 35 U.S.C. 371 of PCT/IB2019/054644, filed 4 Jun. 2019, which claims the benefit of U.S. Provisional Application No. 62/681,567, filed 6 Jun. 2018, the disclosures of which are incorporated by reference in their entireties herein.

BACKGROUND

Sealants are frequently used to deter dental caries that occur due to accumulation of caries-producing microorganisms in a patient's dentition. The areas in the topography of a dentition that are most desirably treated using a sealant are what are commonly referred to as pits and fissures. Sealants are used to fill pits and fissures to achieve a smooth topography, to avoid microorganism accumulation yet not be detrimental to mastication capability.

Conventional dental sealants are provided in either a clear composition or a composition comprising an opacifying filler for imparting a white color. For example, U.S. Pat. No. 4,150,012 teaches a dental composition made from a two-part system, where each of the two parts comprise a polymerizable resin and an opaquing filler; however, the first container comprises a catalyst, while the second container comprises an accelerator reactive with the catalyst in the first container. The dental material is chemically cured (via redox reaction) and provides an opaque dental material when cured.

As another example of a dental sealant, U.S. Pat. No. 6,444,725 teaches an aesthetic dental sealant comprising a hardenable resin, a hardener, and a colorant, the composition has an initial color prior to exposure to actinic radiation and a final (e.g. tooth-like color) color that is different from the initial color subsequent to the composition being exposed to actinic radiation.

SUMMARY

Although imparting color can benefit accurately applying a dental sealant; industry would find advantage in methods of applying dental sealants that minimizes waste of dental sealant, reduces the amount of sealant treatment time, and can provide other benefits.

In one embodiment, a method of applying a two-part dental sealant is described comprising providing a syringe device comprising a cartridge including first and second chamber. The first chamber contains a first part of a dental sealant comprising a (meth)acrylate resin and an oxidizing curing agent. The second chamber contains a second part of a dental sealant comprising a (meth)acrylate resin and a reducing curing agent that reacts with the oxidizing curing agent of the first chamber. The first and/or second part of the dental sealant further comprise a single component or multiple components that neutralize acid and promote remineralization. The syringe device comprises a dispensing nozzle comprising a static mixer and an outlet at one end of the cartridge and a plunger at the opposing end of the cartridge. The plunger includes two rods wherein one end of the rods seals the first and second part of the dental sealant within the chambers and the opposing ends of the plunger rods are connected. The method comprises applying pressure by hand to the plunger thereby conveying the first and second part of the dental sealant through the static mixer and outlet of the dispensing nozzle on a tooth surface.

In another embodiment, a kit for storing and applying a dental sealant is described comprising: i) a syringe device comprising a) a cartridge including first and second chambers,
wherein the first chamber contains a (meth)acrylate resin and an oxidizing curing agent, and
the second chamber contains a (meth)acrylate resin and a reducing curing agent that reacts with the oxidizing curing agent of the first chamber, and the first and/or second chamber further comprises a single component or multiple components that neutralize acid and promote remineralization; b) a plunger at one end of the cartridge, wherein the plunger includes two rods wherein one end of the rods seals the first and second part of the dental sealant within the chambers and the opposing ends of the plunger rods are connected. The kit further comprises
ii) at least one removable dispensing nozzle comprising a static mixer that attaches to the opposing end of the cartridge.

In another embodiment, a two-part dental sealant composition is described comprising
a first part comprising a (meth)acrylate resin and an oxidizing curing agent; and a second chamber part comprising a (meth)acrylate resin and a reducing curing agent that reacts with the oxidizing curing agent of the first chamber; wherein the first and second part each have a viscosity of no greater than 5000 cps and the two-part dental sealant composition further comprises a single component or multiple components that neutralize acid and promote remineralization.

BRIEF DESCRIPTION OF THE DRAWINGS

(FIG. 2 of WO 2016/205181-FN76390)

DETAILED DESCRIPTION OF THE INVENTION

Presently described is a method of applying a dental sealant with a syringe device; a kit for storing and applying a dental sealant comprising a syringe device containing a two-part dental sealant and removable dispensing nozzles that attach to the syringe device; and two-part dental sealant compositions.

Figure 1:
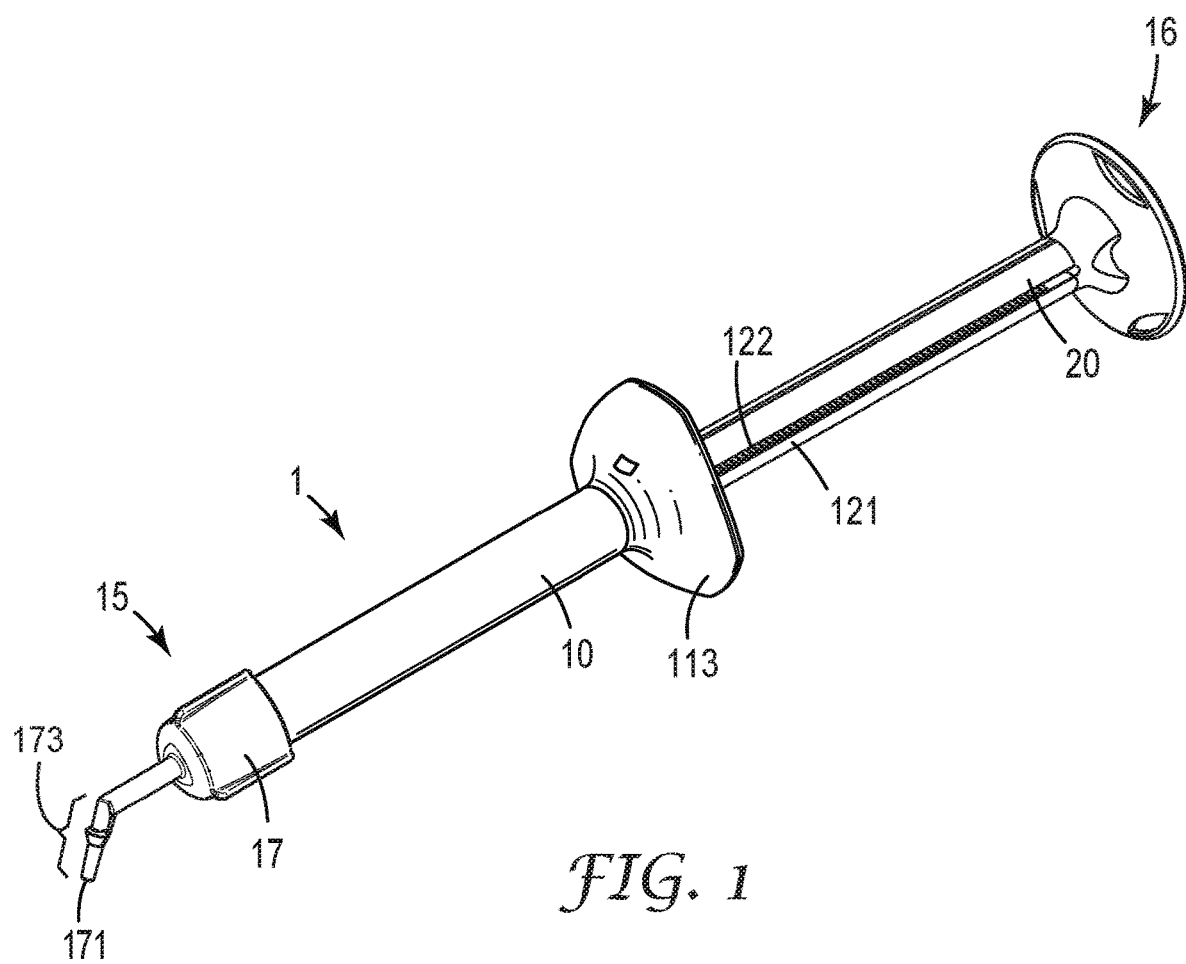
FIG. 1 is a perspective view of an illustrative syringe.

FIG. 1 shows an illustrative syringe device 1 suitable for dispensing a two-part dental sealant material. The syringe device comprises a (e.g. cylindrical) cartridge 10, a plunger 20 and a dispensing nozzle 17.

The cartridge 10 typically has a cylindrical outer shape. In typical embodiments, the cartridge further comprises a finger plate 113. The shape of the finger plate 113 includes flats or supporting points that hinder the cartridge 10 from rolling over when placed on a flat surface. Thus, when the syringe 1 is placed on a flat surface such as a table, the flats of the finger plate 113 of the cartridge 10 can prevent the syringe from rolling off the table.

The cartridge 10 of the syringe 1 is pre-filled with a two-component dental sealant. One part of the two-part dental sealant is contained within a first chamber 111 and the second part of the two-part dental sealant is contained within a second chamber 112.

Figure 2:
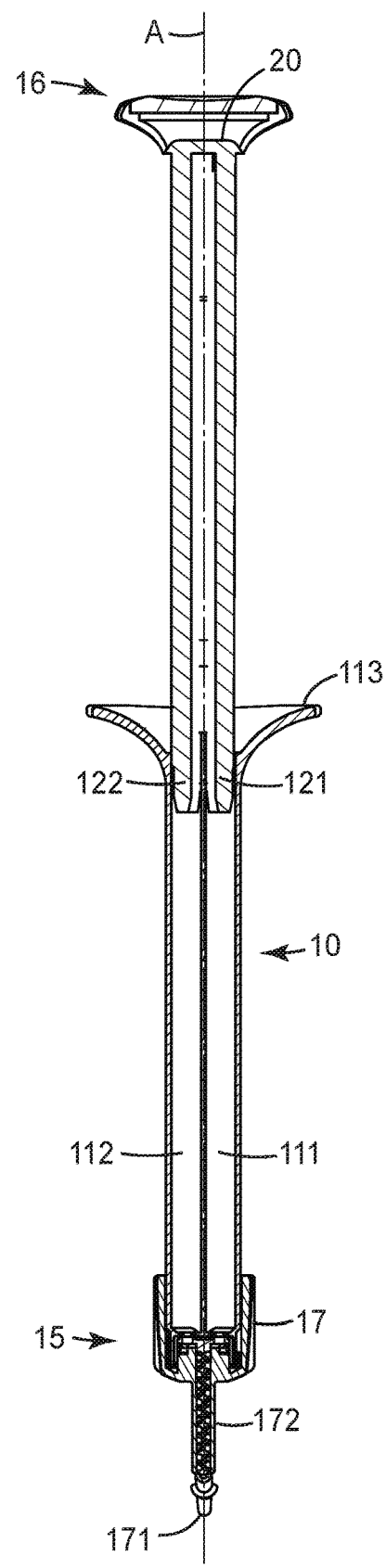
FIG. 2 is a cross-sectional view of an illustrative syringe.

As best shown in the cross-sectional view of FIG. 2, the syringe 1 has a plunger 20 that comprises a first plunger rod 121 and a second plunger rod 122. One end of each rod 121, 122 is configured to seal the first and second part of the dental sealant within the chambers 111 and 112. The opposing ends of the plunger rods are connected at the back end 16 of plunger 20.

The cartridge contains a sufficient amount of two-component dental sealant for sealing one or more teeth. Typically, the amount of two-component dental sealant is sufficient for sealing all the teeth of a single patient. In some embodiments, the amount of two-component dental sealant is sufficient for sealing all the teeth of more than one patient and the removable nozzle is replaced between patients. In typical embodiments, the syringe is pre-filled with the two-part dental sealant composition by the manufacturer. In some embodiments, the (e.g. pre-filled) syringe, two-part dental sealant composition, and one or more removable dispensing nozzles are bundled as a kit for storing and applying dental sealant. The kit typically further comprises instructions for utilizing the kit and attaching the removable nozzle onto the syringe.

To facilitate use in the mouth and to minimize waste of the dental sealant, the syringe device is relatively small. In some embodiments, the total length of the filled syringe (without the nozzle) and prior to engaging the plunger, as shown in FIGS. 1 and 2. is no greater 200 mm, 190 mm, 180 mm, 170 mm, 160 mm, 150 mm or 140 mm. The total length of the filled syringe (without the nozzle) is typically at least 100 mm, 110 mm, 120 mm, or 130 mm. In some embodiments, the total length of the cartridge is typically no greater than 100 mm, 95 mm, 90 mm, 85 mm, 80 mm, or 75 mm. The total length of the cartridge is typically at least 50 mm, 55 mm, 60 mm, or 65 mm. The length of the interior chambers is less than the total length of the cartridge. In some embodiments, the total length of the interior chamber is no greater than 70 mm or 65 mm. The exterior diameter of the cartridge is typically no greater than 15 mm, 14 mm, 13 mm, 12 mm, 11 mm, 10 mm, 9 mm, or 8 mm. The exterior diameter is typically at least 5 mm, 5.5 mm, 6 mm, 6.5 mm, 7 mm or 7.5 mm. The total interior volume of the cartridge is typically no greater than 5, 4.5, 4, 3.5, 3, or 2.5 cc.

In typical embodiment, the first chamber and second chamber have a volume ratio of about 1:1. Other volume ratios could be employed. For example, the volume ratio of the chamber may range from 1:1 to about 2:1 or 3:1.

When the first and second part are intended to be mixed a volume ratio of 1:1, the first and second chamber contain about half the total volume of the cartridge. Thus, the total interior volume of each chamber is typically no greater than 2.5, 2, 1.75, 1.5, or 1.25 cc.

Figure 3:
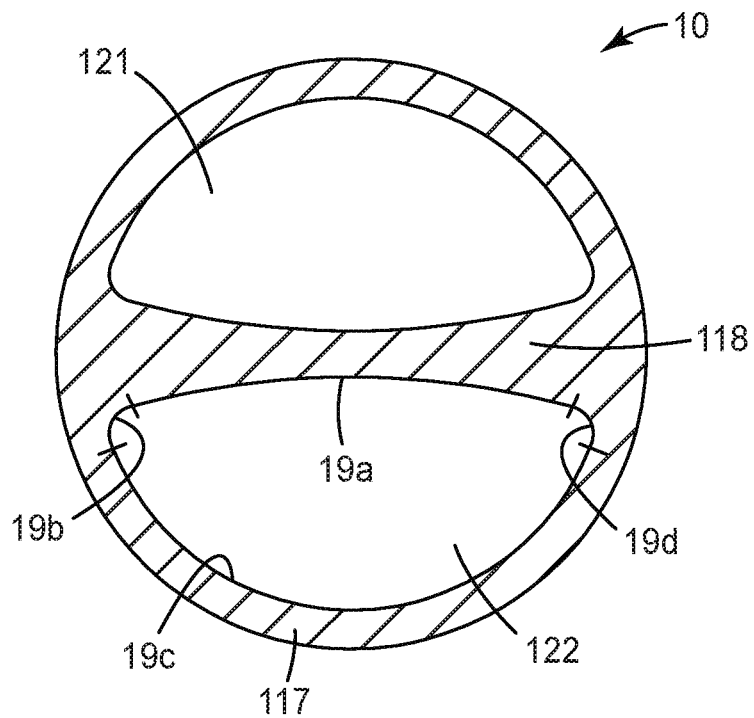
FIG. 3 is a cross-sectional view of an illustrative syringe; (Change to FIG. 3 of US2016/0270879)

FIG. 3 shows a cross-sectional view of the syringe 1 through the cartridge 10. The cartridge 10 has two chambers 111, 112 that extend through the cartridge 10. In some embodiments, the chambers have a substantially D-shaped cross-section, such as described in U.S. Patent Publication No. 2016/0270879; incorporated herein by reference.

In particular, the perimeter of the D-shape is defined by a plurality of circle segments 19a, 19b, 19c and 19d only. (Circle segments 19a, 19b, 19c and 19d correspond to the first, third, second and forth circle segment, respectively.) The circle segment 19a adjacent the separation wall is based on a different radius than the opposite circle segment 19c adjacent the outer wall 17. In particular, the circle segment 19a is based on a larger radius than the circle segment 19c. Thus, on the one hand, a substantial D-shape is achieved but, on the other having a cross-section based on only circular structures allows more reliable sealing compared to a cross-section having one or more straight structures. Further the circle segments 19a, 19b, 19c and 19d join in a manner such that at the joint of two circle segments respective tangents through that joint on each circle segment coincide. Or in other words, the circle segments 19a, 19b, 19c and 19d smoothly merge into one another and together form a closed line defining the perimeter of the cross-section.

In a preferred embodiment the radius of the first circle segment may range from 10 mm to 20, 30, 40, or 50 mm; the radius of the second circle segment may range from 2 mm to 5, 10, 15 or 20 mm; and the radius of the third and fourth circle segment may range from 0.3 mm to 1, 2, or 3 mm. In one embodiment, radius 19a is about 14 mm, radius 19b is about 1 mm and radius 19c, is about 4 mm.

As shown, the two substantial D-shapes are arranged in a mirrored fashion relative to each other so that the cartridge 10 has, on the one end, a generally cylindrical outer shape, and on the other end forms an outer wall 117 with a separation wall 118 having a substantially uniform wall thickness. The substantially uniform wall thickness facilitates for example, manufacturing of the cartridge by injection molding (e.g. of polypropylene).

In some embodiments, each of the plunger rods 121 and 122 are configured for press-fitting into a respective chamber of the cartridge. The plunger rods may comprise a more rigid material than the cartridge. In some embodiments, the plunger rods are injection molded from polypropylene containing 50% glass fibers. The cross-sectional shape of each plunger rod typically corresponds to the cross-sectional shape of the respective chamber. Thus, when the chambers have a substantially D-shaped cross-section, the plunger rods also have a substantially D-shaped cross-section.

In some embodiments, the end portion of the plunger rods 121 and 122 that seal the two-part dental sealant within the chambers are preferably oversized, in particular two-dimensionally enlarged by an offset, relative to the cross-sectional shape of the respective chamber. In one embodiment, each plunger rod 121 and 122 has a skirt-type lip seal, as described in greater detail in previously cited U.S. Patent Publication No. 2016/0270879.

The chambers and plunger rods can have various other designs and cross-sectional shapes such that the two-component dental sealant is sealed within the respective chambers prior to use.

The dispensing nozzle 17 removably attaches to a front end 15 of the cartridge 10. In some embodiments, the nozzle rotatably attaches to the front end of the cartridge 10. The cartridge, nozzle, or combination thereof comprises a valve that can provide or prevent fluid communication between the two-part dental sealant of the cartridge 10 and the dispensing nozzle 17. In some embodiments, the cartridge 10 and the nozzle 17 in combination form a rotary slide valve. Further details concerning valves are described in WO2018/057503 and U.S. Pat. No. 9,427,290; incorporated herein by reference.

Figure 4:
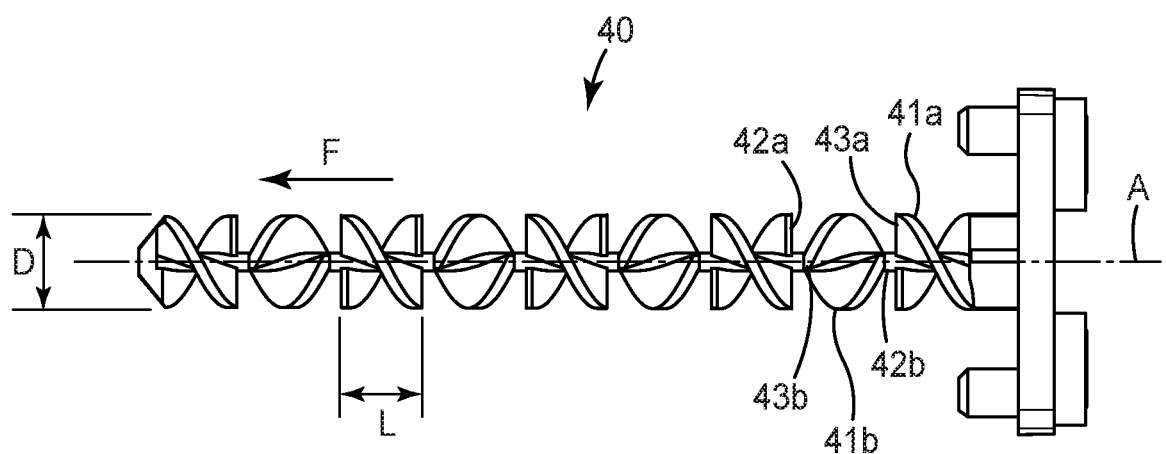
FIG. 4 is a side view of an illustrative static mixer.

The dispensing nozzle 17 further comprises a cannula 172 including a static mixer 40 (not shown in FIG. 1, but depicted in FIG. 2 and FIG. 4).

The volume and design is chosen to maximize mixing and reduce waste. In some embodiments, the total volume of the dispensing nozzle, in the absence of the static mixer, is typically no greater than 0.25, 0.20, 0.15, or 0.10 cc. In some embodiments, the total volume of the dispensing nozzle is no greater than 0.09, 0.08, 0.07, 0.06, 0.05, 0.04, or 0.03 cc. The cannula has an exterior a width of 2, 2.5 or 3 mm and a length of about 75 to 150 mm.

Various static mixers can be utilized. FIG. 4 shows a preferred static mixer 40 that may be arranged within the dispensing nozzle illustrated in FIG. 1 and FIG. 2. Such a static mixer is described in WO2015/205181; incorporated herein by reference. The static mixer 40 has a cascade of mixing elements 41a/41b. Each mixing element 41a/41b is based on a helical shape or a helicoid. The structure of such a helical mixing element can be basically imagined as a planar sheet of material which, held at opposite ends, is twisted or wound by 180 degrees, although other methods (for example injection molding) are typically used to manufacture such a structure. The overall outer shape of such a mixing element 41a/41b is based on a cylindrical helix. Therefore. each mixing element has an outer diameter D. Each mixing element has an entry edge 42a/42b for the material and an exit edge 43a/43b. With respect to a flow F of the dental material through the mixing unit the material enters each mixing element 41a/41b at the entry edge 42a/42b and exits each mixing element 41a/41b at the exit edge 43a/43b. The static mixer 40 has a plurality of mixing elements 41a/41b arranged in sequence. The entry and exit edges 42a/42b, 43a/43b of two adjacent mixing elements 41a/41b are angularly offset relative to each other. Therefore, the flow of the two components of the dental material is divided and partial divisional streams thereof merged multiple times as the dental material flows through the mixing unit 40. Thus, the (e.g. two parts of the) dental material is mixed. The angle of the offset between the entry and exit edges 42a/42b, 43a/43b is measured in a plane perpendicular to a longitudinal axis A of the mixing unit and on a point on that longitudinal axis A. The angle of the offset between the entry and exit edges 42a/42b, 43a/43b in the example is 90 degrees. In other words, the entry and exit edges 42a/42b, 43a/43b of adjacent mixing elements 41a/41b are arranged crosswise relative to each other.

As shown, the mixing unit 40 has right handed mixing elements 41a and left handed mixing elements 41b which are consecutively arranged in an alternate order along the longitudinal axis A. The right and left handed mixing elements 41, 41b differ in the winding direction of the helix on which mixing element 41a/41b is based.

In some embodiments, the mixing elements 41a/41b have an outer diameter D of between 1.5 mm and 1.6 mm. Further, each mixing element has a length L of between 0.6 mm and 1.2 mm, preferably 0.78 mm. The diameter D as well as the Length L is preferably the same for all mixing elements 41a/41b of the mixing unit 40. The specific range of the diameter D of the mixing elements 41a/41b can provide improved mixing.

The dispensing nozzle tip 173 of the dispensing nozzle can be rigid or flexible. It can be formed of a thermoplastic material or may be a metal hollow needle. In some embodiments, the tip of the dispensing nozzle is angular, extending from the cannula at an interior included angle ranging from 90° to 180°. In some embodiments, the interior included angle is at least 95, 100, 105 or 110°. In some embodiments, the interior included angle is no greater than 170, 160, 150, 140, or 130°. In some embodiments, the length of the tip can range from about 5 mm to 15 mm or 20 mm. In some embodiments, the length of the tip is no greater than 14, 13, 12, 11, or 10 mm. The outlet is typically round, having a diameter narrower than the cannula. In some embodiments, the diameter of the outlet is at least 0.5, 0.6, 0.7, or 0.8 mm ranging up to 1, 1.1, 1.2, 1.3, 1.4 or 1.5 mm.

The syringe 1 may optionally include an actuator for stepwise engaging the plunger toward a front end of the syringe. Inclusion of an actuator is useful for dispensing a pre-determined amount (e.g. a single dose) of the dental sealant material. This feature can be useful for applying precisely the correct amount, i.e. a sufficient amount to fill the pits and fissures; yet not an excessive amount such that the presence of the cured sealant can be detected by a patient during chewing. One example of a syringe with an actuator is further described in WO2017/180545; incorporated herein by reference.

During use of the syringe device the nozzle is turned such that the slide valve is open and the fluid contained within the chambers can be conveyed through the nozzle. The (e.g. index and middle) fingers contact the finger plate 113 and the thumb typically presses on the back end 16 of the plunger causing the first plunger rod 121 and a second plunger rod 122 to move towards the front end 15 of the syringe device. Applying pressure by hand to the back end of the plunger thereby conveys the first and second part of the dental sealant through the static mixer and outlet onto (e.g. the enamel of) a tooth surface.

The two components are combined with each other by merging in the static mixer. Each of the components preferably has a viscosity no greater than 5,000 cps at 23° C. when measured according to the test method described in the examples. In some embodiments, the viscosity of each of the components is no greater than 4,500; 4,000; 3,500; or 3,000 cps at 23° C. The viscosity of each of the components is typically at least 200, 300, 400 or 500 cps at 23° C.

Further, the viscosities of the two components are typically similar, for example differ by no more than 50, 45, 40, 35, 30, 25, 20, 15, or 10% of the higher viscosity material. When the viscosity of each components to be mixed and the difference in viscosity is within a suitable range, a sufficiently uniform mixture can be dispensed through the outlet. Further, the components can be conveyed through the static mixer at relatively low extrusion forces. Such low extrusion forces can be typically generated by a manually operated system.

In some embodiments, the method of applying the dental sealant further comprises conditioning the tooth surface, prior to applying the dental sealant. Such conditioning may include (e.g. acid) etching, priming, abrading, or a combination thereof; as known in the art.

Each part of the dental sealant comprises a polymerizable resin. The polymerizable resin is typically a mixture of (meth)acrylate monomers. One common acrylic monomer is described in U.S. Pat. No. 3,066,112. Such acrylic monomer is the reaction product of bisphenol A or other bisphenol with glycidyl methacrylate, the reaction product being commonly referred to in the art as Bis-GMA monomer. Typically, this monomer is combined with various other (e.g. lower molecular weight, lower viscosity) monomers such as di(meth)acrylate monomers (e.g. tetraethyleneglycol dimethacrylate, ethyleneglycol dimethacrylate, triethyleneglycol dimethacrylate, etc.) or monofunctional (meth)acrylate monomers (e.g. methyl methacrylate).

The dental sealant described here comprises a "redox" curing system. In redox processes, reducing agent loses electrons and is oxidized, and the oxidizing agent gains electrons and is reduced. Combining the oxidizing and reducing agent results in the generation of an initiating species (such as free radicals or cations) capable of causing curing (e.g., polymerization and/or crosslinking) of a hardenable resin. Typically, the redox pair are activated at temperatures below about 40° C.

Suitable oxidizing agents include peroxide compounds (i.e., peroxy compounds), including hydrogen peroxide as well as inorganic and organic peroxide compounds (e.g., "per" compounds or salts with peroxoanions). Examples of suitable oxidizing agents include, but are not limited to: peroxides such as benzoyl peroxide, phthaloyl peroxide, substituted benzoyl peroxides, acetyl peroxide, caproyl peroxide, lauroyl peroxide, cinnamoyl peroxide, acetyl benzoyl peroxide, methyl ethyl ketone peroxide, sodium peroxide, hydrogen peroxide, di-tert butyl peroxide, tetraline peroxide, urea peroxide, and cumene peroxide; hydroperoxides such as p-methane hydroperoxide, di-isopropyl-benzene hydroperoxide, tert-butyl hydroperoxide, methyl ethyl ketone hydroperoxide, and 1-hydroxy cyclohexyl hydroperoxide-1.

Other oxidizing compounds include persulfate compounds (e.g. ammonium persulfate, potassium persulfate), perborate compounds (e.g. sodium perborate), perchlorate compounds (e.g. sodium perchlorate), etc.; ozone, ozonides, etc. These oxidizing agents may be used alone or in admixture with one another.

One or more oxidizing agents may be present in the first initiator system in an amount sufficient to provide initiation of the hardening process and the desired rate of cure. The dental sealant typically comprises at least 0.01, 0.02, 0.03. 0.04, 0.05, 0.06, 0.07, 0.08, 0.09 or 1 wt.-% ranging up to 5, 5.5, 6, 6.5, 7, 7.5, 8, 8.5, 9, 9.5 or 10 wt.-% of oxidizing curing agent, based on the total weight of all components of the dental material. In some embodiments, the dental sealant comprises at least 1.5, 2.0, 2.5, 3.0, 3.5, 4.0, 4.5, or 5 wt.-% of oxidizing curing agent.

The first initiator system also includes a reducing agent with one or more functional groups for activation of the oxidizing agent and initiation of hardening. The functional groups are typically selected from amines, mercaptans, or mixtures thereof. If more than one functional group is present, they may be part of the same compound or provided by different compounds.

A preferred reducing agent is a tertiary aromatic amine. An example of a useful tertiary amine is

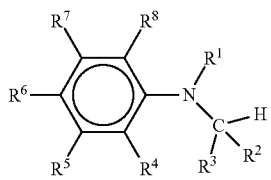

wherein each R group can be H or an organic group that does not adversely effect the initiation of hardening of the dental material. The organic groups generally do not sterically or electronically hinder the function of the reducing agent. Examples of such compounds are disclosed in WO 97/35916, published Oct. 2, 1997.

Preferably $R^1$ is an aliphatic group and $R^2$ and $R^3$ are independently (i.e., they may be the same or different) H, aromatic and/or aliphatic groups (preferably including up to 20 carbon atoms). Preferably, only one of $R^2$ and $R^3$ is an aromatic group. More preferably, $R^1$ is an alkyl group (preferably including up to 10 carbon atoms) optionally substituted with hydroxy groups, and $R^2$ and $R^3$ are H or alkyl groups (preferably including up to 10 carbon atoms) optionally substituted with hydroxyl groups. For certain preferred embodiments, $R^1$, $R^2$, and $R^3$ can also include a polymerizable functional group that will react with the functional groups of the resin. Preferably, at least one of $R^1$, $R^2$, and $R^3$ includes a functional group such as an acrylate, methacrylate, acrylamide, vinyl, or other functional group present in the resins described above.

Preferably, $R^4$, $R^5$, $R^6$, $R^7$, and $R^8$ are independently H or aliphatic groups (preferably including up to 20 carbon atoms). More preferably, $R^4$, $R^5$, $R^6$, $R^7$, and $R^8$ are independently H or alkyl groups (preferably including up to 10 carbon atoms) optionally substituted with hydroxy groups. For certain preferred embodiments, $R^4$, $R^5$, $R^6$, $R^7$, and $R^8$ can also include a polymerizable functional group that will react with the functional groups of the resin. Preferably, at least one of $R^4$, $R^5$, $R^6$, $R^7$, and $R^8$ includes a functional group such as an acrylate, methacrylate, acrylamide, vinyl, or other functional group present in the resins described above.

Particularly preferred aromatic tertiary amines are N,N-bis(2-hydroxyethyl)-p-toluidine (DHEPT), 2-(4-dimethylaminophenyl)ethyl alcohol (DMAPE), 4-tert butyl dimethyl aniline. Other compounds that are suitable include compounds derived from DMAPE with di- or multi-functional acid compounds such as adipic acid, sebacic acid, 1,3,5-benzene tricarboxylic acid, 1,2,4,5-benzene tetracarboxylic acid, and the like, or DMAPE with di-or multi-functional isocyanates such as hexamethylene diisocyanate, isophorone diisocyanate, and desmodur N-330 (a trifunctional isocyanate).

The tertiary amines may be polymerizable. Particularly preferred polymerizable aromatic tertiary amines include, but are not limited to, an adduct of IEM (2-isocyanatoethylmethacrylate) with N,N-bis(2-hydroxyethyl)-p-toluidine (DHEPT-di-IEM or bis-N,N-[2-(2-methacryloloxyethylaminocarbonyloxy)ethyl]-p-toluidine), an adduct of DMAPE with VDM (2-vinyl-4,4-dimethylazlactone) (DMAPE-VDM or 4-[2(2-acrylamido-2-methylpropionyloxy)ethyl)-N,N-dimethlyaniline), an adduct of a methacrylate di-ester with DHEPT (DHEPT-di-ester or bis-N,N-(2-methacryloloxyethyl)-p-toluidine), and an adduct of DHEPT with VDM (DHEPT-di-VDM or bis-N,N-[2-(2-acrylamido-2-methylpropionyloxy)ethyl]-p-toluidine).

Another preferred reducing agent is a mercaptan, that can include aromatic and/or aliphatic groups, and optionally polymerizable groups. Preferred mercaptans have a molecular weight greater than about 200 as these mercaptans have less odor. Particularly preferred mercaptans are isooctylthioglycoate (IOTG) and pentaerythritol tetrakis (3-mercaptopropionate) (PETMP).

The tertiary amines and mercaptans may be used alone or in admixture with one another. For example, the first initiator system can include one tertiary aromatic amine and one mercaptan, two tertiary aromatic amines, two mercaptans, one polymerizable tertiary aromatic amine, and the like. Other reducing agents, such as sulfinic acids, formic acid, ascorbic acid, hydrazines, and salts thereof, can also be used herein to initiate free radical polymerization. Preferably, however, the first initiator system includes a tertiary aromatic amine, a mercaptan, or a mixture thereof. Such reducing agents can function as both a component of the first initiator system and a component of the second initiator system.

When two or more reducing agents are used, they are preferably chosen such that at least one has a faster rate of activation than the other(s).

One or more reducing agents may be present in the first initiator system in an amount sufficient to provide initiation of the hardening process and the desired rate of cure. The dental sealant typically comprises at least 0.01, 0.02, 0.03. 0.04, 0.05, 0.06, 0.07, 0.08, 0.09 or 1 wt.-% ranging up to 5, 5.5, 6, 6.5, 7, 7.5, 8, 8.5, 9, 9.5 or 10 wt.-% of reducing curing agent, based on the total weight of all components of the dental material. In some embodiments, the dental sealant comprises at least 1.5, 2.0, 2.5, 3.0, 3.5, 4.0, 4.5, or 5 wt.-% of reducing curing agent.

Small quantities of transition metal compounds may also be added to accelerate the rate of redox cure. In some embodiments it may be preferred to include a secondary ionic salt to enhance the stability of the polymerizable composition as described in U.S. Pat. Publication No. 2003/0195273 (Mitra et al.). The concentration of oxidizing and reducing curing agent are selected to provide the optimal reaction rate. If the reaction rate is too fast, the dental sealant can prematurely cure in the dispensing nozzle. If the reaction rate is too slow, the total treatment can be extended. In some embodiments, the dental sealant cures within 5, 4, 3, 2, or 1 minute.

The dental sealant may further include a second initiator system. The second initiator system includes one or more initiators commonly used in free radical polymerization. The second initiators are preferably free radical photoinitiators, that may be activated upon irradiation with actinic radiation (using a conventional dental curing light) initiates the polymerization (or hardening) of the free radically polymerizable composition.

Photoinitiators typically can generate free radicals for addition polymerization upon exposure to light energy having a wavelength between 400 and 800 nm. When the dental sealant is photocurable with a conventional dental curing light, the sealant may also further comprise Rose Bengal or other photobleachable colorant such that the dental sealant is colored prior to being cured, yet tooth-colored after curing, such as described in U.S. Pat. No. 6,444,726; incorporated herein by reference. Various photoinitiators suitable for dental compositions are known.

In some embodiments, the dental sealant further comprises a sensitizer. The sensitizer may be co-initiated by the amine reducing agent.

The sensitizer desirably is soluble in the monomer, and is capable of light absorption somewhere within the range of wavelengths of greater than 400 to 800 nanometers, more preferably 400 to about 500 nanometers. The sensitizer may also be capable of sensitizing 2-methyl-4,6-bis(trichloromethyl)-s-triazine, using the test procedure described in U.S. Pat. No. 3,729,313, which is incorporated herein by reference. Preferably, in addition to passing this test, a sensitizer is also selected based in part upon shelf stability considerations.

A sensitizer may also impart a photobleachable color in addition to the color imparted by the dye or pigment colorant. For example, camphorquinone can impart a yellow color to the materials of the invention and Rose Bengal can impart a reddish color to the materials.

Suitable sensitizers can include compounds in the following categories: ketones, coumarin dyes (e.g., ketocoumarins), xanthene dyes, fluorone acridine dyes, thiazole dyes, thiazine dyes, oxazine dyes, azine dyes, aminoketone dyes, porphyrins, aromatic polycyclic hydrocarbons, p-substituted aminostyryl ketone compounds, aminotriaryl methanes, merocyanines, squarylium dyes and pyridinium dyes. Xanthene dyes include those dyes whose molecular structure is related to xanthene and have a Color Index number ranging from 45000-45999. Ketones (e.g., monoketones or alpha-diketones), ketocoumarins, aminoarylketones and p-substituted aminostyryl ketone compounds are preferred sensitizers. For applications requiring high sensitivity, it is preferred to employ a sensitizer containing ajulolidinyl moiety.

For example, a preferred class of ketone sensitizers has the formula:

Suitable ketones of the above formula include monoketones (b=0) such as 2,2-, 4,4- or 2,4-dihydroxybenzophenone, di-2-pyridyl ketone, di-2-furanyl ketone, di-2-thiophenyl ketone, benzoin, fluorenone, chalcone, Michler's ketone, 2-fluoro-9-fluorenone, 2-chlorothioxanthone, acetophenone, benzophenone, 1- or 2-acetonaphthone, 9-acetylanthracene, 2-, 3- or 9-acetylphenanthrene, 4-acetylbiphenyl, propiophenone, n-butyrophenone, valerophenone, 2-, 3- or 4-acetylpyridine, 3-acetylcoumarin and the like. Suitable diketones include aralkyldiketones such as anthraquinone, phenanthrenequinone, o-, m- and p-diacetylbenzene, 1,3-, 1,4-, 1,5-, 1,6-, 1,7- and 1,8-diacetylnaphthalene, 1,5-, 1,8- and 9,10-diacetylanthracene, and the like. Suitable alpha-diketones (b=1 and X=CO) include 2,3-butanedione, 2,3-pentanedione, 2,3-hexanedione, 3,4-hexanedione, 2,3-heptanedione, 3,4-heptanedione, 2,3-octanedione, 4,5-octanedione, benzil, 2,2'-3 3'- and 4,4'-dihydroxylbenzil, furil, di-3,3'-indolylethanedione, 2,3-bornanedione (camphorquinone), biacetyl, 1,2-cyclohexanedione, 1,2-naphthaquinone, acenaphthaquinone, and the like.

The (e.g. first and/or second part of the) dental sealant further comprises a component that promote remineralization, such as a material that releases calcium ions, phosphorus containing ions (e.g. phosphate), fluoride ions, or a combination thereof. In some embodiments, the dental sealant further comprises a compound the releases calcium ions, such as a calcium salt. Examples of calcium salt include calcium glycerol phosphate, calcium carbonate, calcium chloride, calcium caseinate, calcium citrate, calcium glubionate calcium gluceptate, calcium gluconate, calcium hydroxide, calcium hydroxyapatite, calcium lactate, calcium oxalate, calcium oxide, calcium pantothenate, calcium phosphate, calcium polycarbophil, calcium propionate, calcium pyrophosphate, and calcium sulfate. In some embodiments, such as in the case of calcium oxide, the compound that releases calcium ions also neutralizes acid. Thus, a single component promotes remineralization and neutralizes acid. In other embodiments, the compound that releases calcium ions does not neutralize acid. In this embodiment, the dental sealant further comprises a separate component that is a basic material.

In some embodiments, the dental sealant comprises a material that promotes remineralization by release of fluoride ions, such as $AlF_3$, $Na_2AlF_3$, and mixture thereof. Other components that release fluoride ions include silanol treated fluoroaluminosilicate glass fillers, such as described in U.S. Pat. No. 5,332,429. Organic fluoride sources are also suitable, such as those described in U.S. Pat. No. 4,871,786.

In some embodiments, the dental sealant comprises a material that promotes remineralization by release of phosphorus ions. Suitable phosphorus compounds include $P_2O_5$, $AlPO_4$, and mixture thereof. Some salts such as calcium glycerol phosphate release both calcium ions and phosphorous ions.

The concentration of such components that promote remineralization is typically at least 1, 1.5, 2, 2.5, 3, 3.5, 4, 4.5, or 5 wt.-% of the total dental sealant and typically no greater than about 10 wt. %. However, when the component that promote remineralization also neutralizes acid, higher concentrations may be used.

The first and/or second part of the dental sealant further comprises a basic component that neutralizes acid. In the case of dental sealants, it is surmised that the basic component can neutralize acids derived from bacteria or food sources that come in contact with the cured dental sealant.

The component(s) that neutralizes acid are typically combined with the (e.g. second) part of a dental sealant comprising the polymerizable resin and reducing curing agent.

In favored embodiments, the dental sealant comprises an encapsulated material comprising a chemically basic core material. In one favored embodiment, an inorganic shell material surrounding the core. The shell material and thickness of the shell can be selected to permit controlled and/or delayed release or reaction of the basic core material. In some embodiments, the release of the basic core material is utilized for increasing basicity after an extended period of time. Such encapsulated material is further described in US Patent Publication No. 2017/063829; incorporated herein by reference.

Alternatively, the dental sealant may comprise a chemically basic material that is not encapsulated. Thus, the forthcoming description concerning the "basic core" is also applicable to unencapsulated "basic material".

The encapsulated filler comprises a basic core material. The basic (e.g. core) material, as well as the materials (e.g. compounds) from which the core is formed, are generally solid at 25° C. The basic (e.g. core) material can be a single particle or a plurality of smaller associated particles. As used herein, the term "associated" refers to a grouping of two or more primary particles that are aggregated and/or agglomerated. Similarly, the term "non-associated" refers to groupings of two or more primary particles that are free from aggregation and/or agglomeration.

In some embodiments, the basic (e.g. core) material may comprise a plurality of aggregated particles. "Aggregation" or "aggregated" refers to a strong association between primary particles. For example, the primary particles may be chemically bound to one another. The breakdown of aggregates into smaller particles (e.g., primary particles) is typically not achieved during fabrication of the basic (e.g. core) material and encapsulation thereof such that the aggregated basic (e.g. core) particles remain as aggregates. Similarly, the term "non-aggregated" refers to primary particles that are free of strong associations with other primary particles.

In other embodiments, the basic (e.g. core) material may comprise a plurality of agglomerated particles. As used herein, the term "agglomeration" or "agglomerated" refers to a weak association of primary particles. For example, the primary particles may be held together by charge or polarity. The breakdown of agglomerates into smaller particles (e.g., primary particles) can occur during fabrication of the basic (e.g. core) material and encapsulated thereof. Similarly, the term "non-agglomerated" refers to primary particles that are free of weak associations with other primary particles.

The average (e.g. primary, associated, or agglomerated) particle size of the basic (e.g. core) material is typically at least 0.2, 0.5, 1, 2, 3, 4, or 5 micrometers and typically no greater than 1 mm, 750 micrometers, or 500 micrometers, as measured using, for example, a sedimentation analyzer. In some embodiments, the basic (e.g. core) material typically has an average (e.g. primary, associated, or agglomerated) particle size of no greater than 250, 200, 150, 100 or 50 micrometers. In some embodiments, the basic (e.g. core) material typically has an average (e.g. primary, associated, or agglomerated) particle size of no greater than 45, 40, 35, 30, 25, or 20 micrometers. Since the shell is typically thin, the encapsulated material can also fall within the average particle sizes just described.

The core material is basic. Chemically basic materials are materials that donate electrons, accept protons and typically provide hydroxyl ions in aqueous solution.

Material, including cores of the encapsulated material are considered to be basic if they possess or exhibit one or more characteristics described below including comprising a sufficient amount of a high pKa component, providing a basic pH when added to deionized water (according to the test method further described in the examples), or providing a basic pH when added to an acidic buffer (according to the test method further described in the examples).

Basic materials function to react with acids and acidic buffer solutions producing an increase in pH. The change in pH, and the rate of pH change depend on the strength of the basic components, the chemical and physical form of the basic components therein, and the amount of the basic components within the basic (e.g. core) material.

In some embodiments, the basic (e.g. core of the encapsulated) material is strongly basic. Strongly basic materials comprise and are prepared from a sufficient amount of a strongly basic material (e.g. compound), typically having a pKa in the range of about 11-14. Examples of strongly basic compounds include oxides and hydroxides of alkali and alkaline earth metals, as well as strongly basic salts, such as alkali phosphates. Specific examples of strongly basic (e.g. core) compounds include oxides and hydroxides of Na, K, Ca, Sr, and Ba; silicates of Na, K, Ca, Sr, and Ba; and aluminates of Na, K, Ca, Sr, and Ba. Strongly basic silicates and glasses typically comprise at least 1, 2, or 3 moles of strongly basic (e.g. core) compound (e.g. CaO) per mole of silica on a cation molar basis. Likewise, strongly basic aluminate typically comprises at least 1, 2, or 3 moles of strongly basic (e.g. core) compound (e.g. CaO) per mole of alumina on a cation molar basis.

In some embodiments, the strongly basic material can be a heterogenous physical mixture of at least one strongly basic compound in combination with less basic or neutral materials. For example, the strongly basic material may be a physical mixture of silica and sodium hydroxide. Sodium hydroxide is a strongly basic material, having a pKa of 13.8. A 0.1 N aqueous solution of sodium hydroxide has a pH of 13. On a weight percent basis, one gram of a mixture of 96 wt.-% silica and 4% wt.-% sodium hydroxide in a liter of water would provide a 0.1 N aqueous solution of sodium hydroxide. When the encapsulated material is a physical mixture, substantially all the strongly basic compound is accessible upon degradation of the shell. Thus, in this embodiment, the basic (e.g. core) material may comprise a small amount (e.g. at least 1, 2, or 3 wt.-% of a strongly basic material in order to provide a delayed pH of at least 8.5 or 9 in deionized water (according to the test method described in the examples). However, a higher concentration of chemically basic (e.g. core) material may be needed to provide a delayed pH of at least 8.5 or 9 in an acid buffer solution. For example, depending on the pKa of the strongly basic material, the amount of strongly basic material, may be at least 5, 6, 7, 8, 9, or 10 wt.-% of the total encapsulated material.

In other embodiments, the basic (e.g. core of the encapsulated) material is a multicomponent crystalline compound that comprises and is prepared from at least one strongly basic material (e.g. compound) and other components (such as alkaline earth silicates). In yet other embodiments, the basic (e.g. core of encapsulated) material can be characterized as a multicomponent amorphous glass prepared from at least one strongly basic material (e.g. compound). The strongly basic material (e.g. compound) can be distributed homogeneously or nonhomogeneously in the glass structure. When the basic (e.g. core of the encapsulated) material is a fused multicomponent material such as glass, the concentration of strongly basic compound (as can be determined by X-ray fluorescence (XRF) or inductively coupled plasms (ICP)) is typically at least 25, 30, 35, 40, 45, or 50 wt.-% ranging up to 75 wt.-% or greater based on the total basic (e.g. core) material.

In some favored embodiments, the basic (e.g. core) material comprises and is prepared from CaO, having a pKa of 11.6. CaO can be utilized to provide both a delayed increase in pH in combination with providing a source of calcium ions. The amount of CaO is typically at least 5, 10, 15, 20, or 25 wt.-% and can range up to 75 wt.-% or greater. The amount of Ca is about 71% of such values. Specific examples of strongly basic multicomponent (e.g. core) materials comprising CaO include Portland cements (reported to contain 60-70% wt.-% CaO); tricalcium silicate (containing about 75 wt.-% CaO); and bioactive glass, as can be obtained from 3M Advanced Material Division (containing from about 25 wt.-% of CaO, and about 25 wt.-% of $Na_2O$).

In other embodiments, the basic (e.g. core of the encapsulated) material is weakly basic. Weakly basic materials comprise a substantial amount of at least one material (e.g. compound) having a pKa in the range of at least 8, but less than 11. In some embodiments, the weakly basic materials have a pKa of at least 8.5, 9, 9.5, 10, 10.5. Examples of weakly basic (e.g. core) compounds include oxides of Cu, Zn, and Fe as well as and weakly basic salts, such as NaF, Ca acetate, and hydrogen phosphates.

Alternatively, a weakly basic (e.g. core) material may comprise or be prepared from a smaller amount of a strongly basic compound. A weakly basic (e.g. core) material alone cannot typically provide a sufficient amount of hydroxyl ion to adequately increase the pH of an acidic solution. However, a weakly basic (e.g. core) material alone may provide a sufficient amount of hydroxyl ion to adequately increase the pH of water. Further, (e.g. encapsulated) weakly basic (e.g. core) materials can be used in combination with (e.g. encapsulated) strongly basic (e.g. core) materials.

The (e.g. encapsulated) basic material is typically not a reducing agent of a redox curing system. Encapsulation of a reducing agent would delay the redox curing reaction. Further, since reducing agents are typically weak bases utilized in relatively small concentrations, encapsulated reducing agent alone would not provide the desired increase in pH.

In favored embodiments, the basic (e.g. core) material further comprises and is prepared from one or more neutral compounds, defined herein as having a pKa of at least 6, 6.5 or 7, and less than 8. In some embodiments, such neutral compounds exhibit low solubility in deionized water, and/or a weak acid solution, and/or a weak base solution. Weak acid solutions typically have a pH of less than 7, but greater than 4. Weak base solutions typically have a pH of greater than 7, but less than 10. By low solubility, it is meant that less than 100 grams per liter (i.e. 10 wt-%) dissolve. In some embodiments, less than 50, 25, 5, or 1 gram dissolves per liter. Neutral compounds include for example silica, zirconia, titania, alumina, and combinations thereof. Although a pKa greater than 7 is slightly basic, such basicity is less than that of weakly basic (e.g. core) materials and significantly less than that of strongly basic (e.g. core) materials, as previously described.

When the (e.g. core) material comprises and is prepared solely from basic materials (e.g. compound(s) or a combination of basic materials with neutral materials, the basicity of the (e.g. core) material can be estimated based on the weight of the components). Thus, the (e.g. core) material comprises the amount of basic material (e.g. compound) as previously described. However, when the core material further comprises acidic materials (e.g. compounds) it can be more difficult to estimate the basicity. Particularly for embodiments wherein it is difficult to estimate the basicity of a (e.g. core) material based on its composition or compositional analysis, the basicity of the basic (e.g. core) material or encapsulated core material can be defined by a change in pH of a specified amount of material in deionized water or in an acidic (e.g. buffer) solution. These tests can also be used to verify that a (e.g. core) material or encapsulated core material is in fact basic.

For example, fluoroaluminosilicate (FAS) glass is a homogeneous glass structure prepared from about 19 wt.-% of a strongly basic compound (SrO) with the remainder being prepared from neutral ($SiO_2$) and other compounds. When tested in deionized water, according to the test method described in previously cited 78772, FAS glass decreases the pH to 6.5 within 15 minutes and thus would be considered a weakly acidic core material.

In some embodiments, the basicity of the (e.g. core) material or encapsulated core material can be determined by a change in pH of a specified amount (0.25 g) of material in 25 g of deionized water. An unencapsulated basic (e.g. core) material typically changes the pH of deionized water from neutral to a pH of at least 8.5 or 9. This typically occurs within 1, 2, 3, 4, or 5 minutes, but may take up to an hour or 24 hours.

In a favored embodiment, the basicity of the basic (e.g. core) material or encapsulated material can be determined by a change in pH of a specified amount (0.25 g) of material in a buffer solution, a solution of 15 g of deionized water and 10 g of an aqueous potassium acid phthalate buffer solution adjusted to a pH of 4.00 at 25° C. (with hydrochloric acid) (e.g. Buffer BDH5018) having a pH of 4. This test will be referred to herein as "the buffer test." When a strongly basic (e.g. core) material or encapsulated material is subjected to the buffer test, it also can reach a pH of at least 8.5 or 9. It is appreciated that a higher amount of hydroxyl ion is needed to change an acidic solution to a basic pH as compared to deionized water. Thus, it can take longer for this pH change to occur as compared to the same material in deionized water. In some embodiments, such pH change occurs in 5, 10 or 15 minutes, but may take up to 1 hour or 24 hours.

Weakly basic (e.g. core) materials may provide a small increase in pH when tested according to the buffer test. For example, the pH may increase from 4 to 5. However, a weakly basic (e.g. core) material does not provide a sufficient amount of hydroxyl ions to cause the pH to reach a pH of at least 8.5 or 9 when tested according to the buffer test.

Thus, an encapsulated basic core material when added to water or buffer as described herein initially (i.e. immediately after submersion of the material in water or buffer) does not change the pH, but then the pH increases at various rates depending on the shell and basic core material.

In some embodiments, the basic (e.g. core) material is curable or self-setting when mixed with water, such as in the case of various natural and synthetic cements. Conventional natural (e.g. Portland) and synthetic cements typically comprises a major amount of calcium silicate (e.g. $3CaO—SiO_2$, $2CaO$—$SiO_2$) alone or in combination with one or more calcium aluminates (e.g. $3CaO$—$Al_2O_3$, $4CaO$—$Al_2O_3$—$Fe_2O_3$).

In some embodiments, the encapsulated material is an encapsulated (e.g. dental) filler.

Encapsulated (e.g. dental) fillers can comprise a substantial amount of neutral metal oxide that has low solubility as previously described in water or acidic solutions having a pH of 3-4. Neutral metal oxides include for example silica, zirconia, titania, and alumina. The amount of neutral metal oxide(s) can be at least 10, 15, 20, 25, 30 wt.-% ranging up to 50, 60, 70, 80, or 90 wt.-% of the total weight of the basic (e.g. core) material. Calcium silicates and encapsulated calcium silicates may also be characterized as fillers due to their silica content.

The dental sealant comprises a material that promotes remineralization, as previously described. These materials can be present in the core of the encapsulated filler, can be provided as a second filler such as FAS glass, or can be provided as a separate component in the hardeneable dental sealant composition.

In some embodiments, the core or second filler material comprises and is prepared from fluoride compounds such as $AlF_3$, $Na_2AlF_3$, and mixture thereof, in an amount ranging from about 5 to 40 wt.-%. In some embodiments, the amount of $AlF_3$ ranges from 10 to 30 wt.-% of the core or second filler material. In some embodiments, $Na_2AlF3$ ranges from 2 to 10 wt.-% of the core or second filler material.

In some embodiments, the core or second filler material comprises and is prepared from phosphorus compounds such as $P_2O_5$, $AlPO_4$, and mixture thereof, in an amount ranging from 2 to 25 wt.-%. In some embodiments, the amount of $P_2O_5$ ranges from 2 to 15 wt.-% of the core or second filler material. In some embodiments, the amount of $AlPO_4$ ranges from 2 to 10 wt.-% of the core or second filler material.

The basic (e.g. core) material can be encapsulated with any suitable method. In some embodiments, the basic (e.g. core material is encapsulated in an inorganic shell comprising a metal oxide with any suitable method, such as vapor deposition, atomic layer deposition (ALD), sputtering, or evaporation, which are techniques well known in the art.

The shell material may be a weakly basic material. However, the basicity of the shell material is not sufficient to produce the desired pH change, particularly according to the previously described buffer test or disk buffer test (as subsequently will be described).

In some embodiments, the shell, or in other word encapsulant, has an average thickness of at least 5, 10, 15, 20, or 25 nm. The thickness of the shell may range up to 250, 500, 750, or 1000 nm (1 micrometer). In some embodiments, such as in the case of encapsulated dental filler, the thickness of the shell typically ranges up to 50, 75, 100, 150, or 200 nm.

On a wt.-% basis the shell material is typically at least 0.1, 0.2, 0.3, 0.4, or 0.5 wt.-% of the total encapsulated material. The amount of shell material on a wt.-% basis can range up to 15 or 20 wt.-% of the total encapsulated material, but is more typically no greater than 10, 9, 8, 7, 6, or 5 wt.-%. In some embodiments, the amount of shell material on a wt.-% basis is no greater than 4.5, 4, 3.5, 3, 2 or 1 wt.-%.

In preferred embodiments, the shell material and thickness of the shell is selected to permit controlled and/or delayed release or reaction of the basic core material.

In preferred embodiments, the shell is initially impermeable (i.e. material from a composition and core material cannot interact via simple diffusion through the shell). Interaction occurs after the shell is changed via interaction with other materials (e.g. degraded, corroded, or dissolved). Compositions (e.g. two-part compositions) can be designed that comprise components, such as water or acid, that degrade the shell. In other embodiments, shell degradation can take place due to coming in contact with water or an acidic component during use. In this embodiment, the source or water or acidic component can be a biological fluid (e.g. saliva or water retained in soft tissue surrounding a tooth or bone).

In some embodiments, the concentration of (e.g. encapsulated) basic material is typically at least 2, 3, 4, 5, 10, 15, 20, 25, 30, 35, 40, 45, 50, 55, 60, or 65 wt.-% ranging up to 100% of the second part of the hardenable dental sealant composition. The total hardenable (e.g. dental composition) comprises half such concentration of (e.g. encapsulated) basic material. Hence, the concentration of (e.g. encapsulated) basic material is typically at least 1, 1.5, 2, 2.5, 5, 7.5, 10, 12.5, 15, 17.5, 20, 22.5, 25, 27.5, 30, or 32.5 wt.-% ranging up to 50 wt.-% of the total hardenable dental sealant compositions. The concentration can be selected based on the strength of the basic (e.g. encapsulated) material and the intended properties of the dental sealant composition.

With reference to Tables 4-7 of previously cited 78772WO003, in one embodiment, unencapsulated (e.g. Portland cement or tricalcium silicate) basic material provides a basic pH (e.g. at least 8.5, 9, 9.5. 10, or 10.5) within 1 minute when subjected to the previously described buffer test. However, encapsulated (e.g. Portland cement or tricalcium silicate) basic material does not provide a basic pH (e.g. at least 8.5, 9, 9.5. 10, or 10.5) for 2, 3, 4, 5, 6, 7, 8, 9 or 10 minutes or greater according the buffer test. In some embodiments, the encapsulated (e.g. Portland cement) basic material does not provide a basic pH (e.g. at least 8.5, 9, 9.5. 10, or 10.5) for 15, 20, 25, 30, 35, 40, or 45 minutes. In some embodiments, the encapsulated (e.g. Portland cement) basic material does not provide a basic pH (e.g. at least 8.5, 9, 9.5. 10, or 10.5) for 100, 200, or 300 minutes.

In another embodiment, unencapsulated (e.g. bioactive glass) basic material provides a basic pH (e.g. at least 8.5, 9, 9.5. 10, or 10.5) within 5 minutes when subjected to the previously described buffer test. However, encapsulated (e.g. bioactive glass) basic material does not provide a basic pH (e.g. at least 8.5, 9, 9.5. 10, or 10.5) for 30-40 minutes according the buffer test.

In another embodiment, unencapsulated (e.g. Portland cement) basic material provides a basic pH of 11.5 within 20 seconds when tested in deionized water. However, encapsulated (e.g. Portland cement) basic material provides a basic pH of at least 8.5 within 20 second when tested in deionized water. In another embodiment, unencapsulated (e.g. bioactive glass) basic material provides a basic pH of 10.5 within 20 seconds when tested in deionized water. However, encapsulated (e.g. bioactive glass) basic material provides a basic pH of at least 9.8 within 20 second when tested in deionized water. Thus, the change in pH of an acidic (e.g. buffer) solution can occur at a significantly slower rate than deionized water.

In preferred embodiments, the delayed release or reaction of the basic (e.g. core) material is utilized for increasing basicity of a hardened dental sealant material, and can neutralize acid formed in the oral environment proximate the cured dental sealant at a later time. Unencapsulated strongly basic material can produce a desirably large (yet undesirably rapid) increase in pH. The same encapsulated basic material can produce the desired increase in pH but after a longer duration of time or provide a slow, continuous release of basic material (e.g. hydroxyl ion).

The basicity of a (e.g. biological) carrier material, such as a hardened dental sealant composition comprising encapsulated or unencapsulated basic material can be evaluated by measuring the pH change of a disk (3.1 mm by 1.3 mm in height) of hardened (i.e. cured) material submerged in 1.5 ml of 10 mM Na$_2$HPO$_4$ (commonly known as PBS) buffer solution contained within a 2 ml plastic centrifuge tube. PBS buffer can be prepared by dissolving 8 g NaCl, 0.2 g of KCL, 1.44 g of Na$_2$HPO$_4$, and 0.24 g of KH$_2$PO$_4$ in 800 ml distilled H$_2$O, adjusting the pH to 7.4 with HCl, adjusting the volume to 1 L with additional distilled water, and sterilizing by autoclaving. This test will subsequently be referred to as the disk buffer test.

A representative two-part hardenable dental sealant composition that may be utilized for the disk buffer test is further described in the forthcoming examples.

In some embodiments, the hardened dental sealant composition comprising the encapsulated or unencapsulated basic material increases the pH of the buffer solution by at least 0.05, 0.10, 0.15, 0.20, 0.25, or 0.30 within 15 or 39 hours.

The hardened dental sealant compositions are initially neutral (pH of 7-7.5) in water and increase in basicity (pH of at least 8, 8.5, 9, 9.5, 10, 10.5 or 11) after various periods of time ranging from 1 hour to 1 day and in some embodiments ranging up to 2, 3, 4, 5, 6, or 7 days, or greater. However, when the released base neutralizes acid present in the oral environment, the hardened dental sealant composition may remain neutral (pH of 7-7.5) due to the neutralization reaction proceeding at a rate equal to the rate of release of the basic (e.g. core) material.

In one embodiment, the encapsulated or unencapsualted basic material provides a basic pH (e.g. at least 8.5, 9, 9.5. 10, or 10.5) within 46, 72, 100, 147, 260, 360 or 500 hours for compositions comprising greater than 16.25 wt.-% of encapsulated basic material.

The dental sealant composition may optionally comprise additional adjuvants suitable for use in the oral environment, including flavorants, anti-microbials, fragrance, stabilizers, viscosity modifiers, rheology modifiers, inhibitor, and ultraviolet (UV) absorbers (for embodiments wherein the dental sealant is not cured by exposure to UV light. Other suitable adjuvants include agents that impart fluorescence and/or opalescence.

In some embodiments, the cured dental sealant has a tooth-like white appearance. In this embodiment, at least one of the parts of the dental sealant typically further comprises an opacifying filler. Suitable fillers include for example titania, zirconia, alumina, or silica. The average particle size of the opacifying filler is typically at least 0.1 or 0.2 microns and ranges up to 0.7 or 1 micron. In some embodiments, an encapsulated material that comprises a basic core material and an inorganic shell material, as will subsequently be described, is the sole or primary opacifying filler.

The concentration of opacifying filler is typically at least 0.05, 0.10, 0.15, 0.2% by weight and may range up to 5% by weight.

The preferred amount of opacifying filler will vary depending upon the particle size distribution and the refractive index of the opacifying filler and the cured resin system. The greater the difference in index of refraction between the filler and the cured resin, the more efficient the filler is in terms of opacifying.

In typical embodiments, a suspending agent may be used, such as fumed silica. Fumed silica is commercially available as the trade designation "Cab-O-Sil" from Cabot Corporation and as the trade designation "Aerosil" from Degussa, Inc. The suspending agent can thicken the composition and thereby increase the viscosity.

The concentration of suspending agent is typically at least 0.05, 0.10, 0.15, 0.2% by weight and may range up to 5% by weight. The concentration of suspending agent may be reduced when higher concentrations of basic materials are employed in order to maintain a sufficiently low viscosity.

In typical embodiments, the opacifying filler and suspending agent comprise a hydrophobic (e.g. organosilane) surface treatment. The procedure described in U.S. Pat. No. 3,066,112, incorporated herein by reference, may be used to treat the filler. A useful reactive organosilane for this purpose is gamma-methacryloxypropyltrimethoxysilane ("A-174", commercially available from Union Carbide).

The dental sealant compositions described herein are typically prepared by first mixing together the polymerizable resin with the oxidizing or reducing agent; as well as other optional additives. Then the opacifying filler and suspending agent are mixed in under conditions of high shear until a homogeneous dispersion is obtained.

The invention is illustrated by the following examples.
Materials
Camphorquinone (CPQ), Benzoyl peroxide—LUPEROX A75 (BPO), 2-(4-Dimethylamino)phenyl)ethanol (DMAPE), Triethylene glycol dimethacrylate (TEGDMA), and Bisphenol A glyceroate dimethacrylate (BisGMA) were obtained from Sigma-Aldrich. 2,6-Ditert-butyl-4-methylphenol (BHT) was obtained from PMC Specialties Incorporated, Cincinnati, Ohio.
Fumed silica (AEROSIL R972) was obtained from Evonik Corporation, Piscataway, N.J.
Portland Cement: White Portland Cement (Federal White Type 1, ASTM Designation C150) was purchased from Federal White Cement, Woodstock, Ontario, Canada. The major components of the composition as reported by the manufacturer are tricalcium silicate (3CaO—SiO$_2$), dicalcium silicate (2CaO—SiO$_2$), tricalcium aluminate (3CaO—Al$_2$O$_3$), tetracalcium aluminoferrite (4CaO—Al$_2$O$_3$—Fe$_2$O$_3$), magnesium oxide, calcium oxide, potassium sulfate, and sodium sulfate. Portland cement is a strongly basic material comprising multiple components. Each major component (excluding the minor components of magnesium oxide, potassium sulfate, and sodium sulfate) contains a significant amount of a strong base (CaO). Portland cement typically contains about 61%-69% CaO, about 18%-24% SiO$_2$, about 2%-6% Al$_2$O$_3$, about 1%-6% Fe$_2$O$_3$, about 0.5%-5% MgO.
Calculations
The following equations 1-6 were used to calculate the shell thickness, wt.-% of core material, and wt.-% shell material for the Encapsulated Materials prepared by the processes described in Examples 1-2. In the calculations, the total surface area of the core material was determined by representing the particles of the core material powder as spheres (surface area=$4\pi(d/2)^2$, volume=$(4/3)(\pi)(d/2)^3$.

$$ST_{em} + \frac{V_{mo}}{SA_c} \qquad \text{Equation 1}$$

$ST_{em}$ (cm)=Shell Thickness of Encapsulated Material.
$V_{mo}$ (cm$^3$)=Volume of Metal Oxide a prepared by APCVD process.
$SA_c$ (cm$^2$)=Total Surface Area of Core Material Powder.

$$V_{mo} = \frac{FR_{cg} * CT * MW_{mo} * CA * \% P * EDE}{1000\left(\frac{cm^3}{L}\right) * 22.4\left(\frac{L}{mol}\right) * D_{mo}} \quad \text{Equation 2}$$

$FR_{cg}$ (cm³/min)=Flow Rate of Carrier Gas (for Al₂Me₆, TiCl₄, SiCl₄).
CT (min)=Coating Time.
CA=Cations per Mole of Precursor Material.
$MW_{mo}$ (g/mol)=Molecular Weight of Metal Oxide per Mole of Cation (for Al₂O₃ $MW_{mo}$=51 g/mol, for TiO₂ $MW_{mo}$=80 g/mol, for SiO₂ $MW_{mo}$=60 g/mol).
$D_{mo}$ (g/cm³)=Density of Metal Oxide (for Al₂O₃ $D_{mo}$=3.0, for TiO₂ $D_{mo}$=3.0, for SiO₂ $D_{mo}$=2.2).
% P=the molar percentage of metal oxide precursor contained in the carrier gas (% P for Al₂Me₆=1.33%, % P for TiCl₄=1.33%, % P for SiCl₄=35.7%).
EDE=Estimated Deposition Efficiency of the APCVD process used in the examples (EDE for Al₂O₃=0.5, EDE for TiO₂=0.6, EDE for SiO₂=0.4).

$$SA_c = N_{cp} * 4\pi\left(\frac{d}{2}\right)^2 \quad \text{Equation 3}$$

$N_{cp}$=Number of Core Material Powder Particles.

$$N_{cp} = \frac{M_{cp}}{D_{cp} * \frac{4}{3}\pi\left(\frac{d}{2}\right)^3} \quad \text{Equation 4}$$

Mcp (g)=Amount of Core Powder Material used in APCVD process (bioactive glass, Portland cement, tricalcium silicate).
Msm (g)=Amount of Metal Oxide deposited by APCVD process (Al₂O₃, TiO₂, SiO₂).
Msm (g)=$V_{mo}*D_{mo}$
$D_{cp}$ (g/cm³)=Density of Core Powder Material (for bioactive glass Dcp=2.65, for Portland cement Dcp=3.11).
d (cm)=Diameter of Core Particle.
Equations 5 and 6—Weight Percentages (wt.-%) of Encapsulated Materials:

$$\text{weight percent Shell} = 100 * \frac{Msm(g)}{[Msm(g) + Mcp(g)]}$$

weight percent Core = (100 − weight percent Shell).

Measurements

Viscosity measurements were determined using a Brookfield DV-I+ Viscometer with a HELIPATH stand and type-A T-bar spindle (AMETEK Brookfield, Middleboro, Mass.). The measurements were performed at 23° C. and shear rate of 100 s⁻¹. Test results were obtained when the viscosity measurement stabilized (typically within 0.5-2 minutes). Viscosities are reported in centipoise (cP).

EXAMPLE 1

Encapsulated Material 1 (PC Core and AO Shell)

Portland cement (PC) was encapsulated with an aluminum oxide (AO) based material using atmospheric pressure chemical vapor deposition (APCVD). The Portland cement powder was coated by reacting trimethyl aluminum (obtained from Strem Chemicals, Newburyport, Mass.) and dispensed from a stainless steel bubbler) with water vapor in a fluidized bed reactor. The reactor was a glass frit funnel tube (12 cm diameter, 30 cm height). The reactor had an extended inlet tube from below the frit routed parallel to the body of the reactor, and an extended top area above the frit to allow the desired reactor height and fittings for a precursor injector tube and an exhaust outlet. Temperature was controlled at 180° C. using an oil bath. Nitrogen carrier gas was used with standard bubbler configurations for liquid precursors. The bubblers were maintained at an ambient temperature of about 22° C. The flow rate through the trimethyl aluminum (TMA) bubbler was 1773 cm³/minute. The flow rate through the water bubbler was 5307 cm³/minute. The total coating time was 120 minutes. The amount of Portland cement added to the reactor was 800 g and the particle size of the Portland cement powder was 20 microns.

Prior to adding to the reactor, fine particles and coarse particles were removed from the Portland cement sample using an AVEKA CCE centrifugal air classifier Model 100 (AVEKA CCE LLC, Cottage Grove, Minn.). In the first step, a coarse tail totaling about 24% of the initial sample was removed and then in the second step a fines tail of about 25% was removed from the remaining sample. The resulting Portland cement powder had a mean particle size of 20 microns (as determined using a Coulter Counter Multisizer 3 (Beckman Coulter Company, Brea, Calif.).

Encapsulated Material 1 was calculated to have a shell thickness of 46 nm. The calculated weight percentages (wt.-%) were 98.8 wt.-% core material and 1.2 wt.-% shell material.

EXAMPLE 2

Encapsulated Material 2 (PC Core and AO Shell)

Portland cement (PC) was encapsulated with an aluminum oxide (AO) based material using atmospheric pressure chemical vapor deposition (APCVD). The Portland cement powder was coated by reacting trimethyl aluminum (obtained from Strem Chemicals and dispensed from a stainless steel bubbler) with water vapor in a fluidized bed reactor. The reactor was a glass frit funnel tube (12 cm diameter, 30 cm height). The reactor had an extended inlet tube from below the frit routed parallel to the body of the reactor, and an extended top area above the frit to allow the desired reactor height and fittings for a precursor injector tube and an exhaust outlet. Temperature was controlled at 180° C. using an oil bath. Nitrogen carrier gas was used with standard bubbler configurations for liquid precursors. The bubblers were maintained at an ambient temperature of about 22° C. The flow rate through the trimethyl aluminum (TMA) bubbler was 2670 cm³/minute. The flow rate through the water bubbler was 8032 cm³/minute. The total coating time was 190 minutes. The amount of Portland cement added to the reactor was 1500 g and the particle size of the Portland cement powder was 20 microns.

Prior to adding to the reactor, fine particles and coarse particles were removed from the Portland cement sample using an AVEKA CCE centrifugal air classifier Model 100 (AVEKA CCE LLC). In the first step, a coarse tail totaling about 24% of the initial sample was removed and then in the second step a fines tail of about 25% was removed from the remaining sample. The resulting Portland cement powder had a mean particle size of 20 microns (as determined using a Coulter Counter Multisizer 3 (Beckman Coulter Company).

Encapsulated Material 2 was calculated to have a shell thickness of 58 nm. The calculated weight percentages (wt.-%) were 98.5 wt.-% core material and 1.5 wt.-% shell material.

EXAMPLE 3

The composition of Paste AA-1 is reported in Table 1 (each component reported in wt.-%). Paste AA-1 was prepared in bulk. BisGMA and TEGDMA were combined (1:1 by weight) and stirred until homogeneous. The BisGMA/TEGDMA mixture was combined with BPO and CPQ in a mixing cup. The filled cup was placed in a FlackTek SPEEDMIXER (FlackTek Incorporated, Landrum, S.C.) and the contents were mixed at 2400 rpm until a homogeneous mixture was achieved. Fumed silica (AEROSIL R972) was added to the cup. The cup was placed in a FlackTeK SPEEDMIXER and the contents were mixed at 2400 rpm until a homogeneous mixture of Paste AA-1 was achieved. The viscosity of Paste AA-1 was 1130±9 cP (at 23° C. and shear rate of 100 $s^{-1}$).

The composition of Paste BB-1 is reported in Table 2 (each component reported in wt.-%). BisGMA and TEGDMA were combined (1:1 by weight) and stirred until homogeneous. The BisGMA/TEGDMA mixture was combined with DMAPE and BHT in a mixing cup. The filled cup was placed in a FlackTek SPEEDMIXER and the contents were mixed at 2400 rpm until a homogeneous mixture was achieved. Fumed silica (AEROSIL R972) was added to the cup. The cup was placed in a FlackTeK SPEEDMIXER and the contents were mixed at 2400 rpm until a homogeneous mixture was achieved. Encapsulated Material 1 was added to the cup. The cup was placed in a FlackTeK SPEEDMIXER and the contents were mixed at 2400 rpm until a homogeneous mixture of Paste BB-1 was achieved. The viscosity of Paste BB-1 was 1450±12 cP (at 23° C. and shear rate of 100 $s^{-1}$).

TABLE 1

Composition of Paste AA-1

| Component | Weight Percent (wt.-%) in the Composition |
| --- | --- |
| BisGMA/TEGDMA (1:1 by weight) | 93.97 |
| BPO | 0.94 |
| CPQ | 0.09 |
| Fumed Silica (AEROSIL R972) | 5.0 |

TABLE 2

Composition of Paste BB-1

| Component | Weight Percent (wt.-%) in the Composition |
| --- | --- |
| BisGMA/TEGDMA (1:1 by weight) | 83.66 |
| DMAPE | 1.25 |
| BHT | 0.09 |
| Fumed Silica (AEROSIL R972) | 5.0 |
| Encapsulated Material 1 | 10.0 |

EXAMPLE 4

The composition of Paste BB-2 is reported in Table 3 (each component reported in wt.-%). BisGMA and TEGDMA were combined (1:1 by weight) and stirred until homogeneous. The BisGMA/TEGDMA mixture was combined with DMAPE and BHT in a mixing cup. The filled cup was placed in a FlackTek SPEEDMIXER and the contents were mixed at 2400 rpm until a homogeneous mixture was achieved. Fumed silica (AEROSIL R972) was added to the cup. The cup was placed in a FlackTeK SPEEDMIXER and the contents were mixed at 2400 rpm until a homogeneous mixture was achieved. Encapsulated Material 2 was added to the cup. The cup was placed in a FlackTeK SPEEDMIXER and the contents were mixed at 2400 rpm until a homogeneous mixture of Paste BB-1 was achieved.

Pastes AA-1 and BB-2 were equilibrated in a chamber at 37° C. and then combined in an approximately 1:1 volume ratio on a mixing pad. The resulting sealant composition hardened after two minutes.

When Pastes AA-1 and BB-2 were combined in a 1:1 volume ratio on a mixing pad at room temperature conditions (about 23° C.) without use of a curing light (dark curing), the sample was not hardened after two minutes.

Alternatively, Pastes AA-1 and BB-2 were combined in a 1:1 volume ratio on a mixing pad at room temperature conditions (about 23° C.) and immediately cured using an Elipar™ DeepCure-S LED curing light (3M Oral Care, Maplewood, Minn.). The sealant composition hardened after exposure to the light for 10 seconds.

TABLE 3

Composition of Paste BB-2

| Component | Weight Percent (wt.-%) in the Composition |
| --- | --- |
| BisGMA/TEGDMA (1:1 by weight) | 83.66 |
| DMAPE | 1.25 |
| BHT | 0.09 |
| Fumed Silica (AEROSIL R972) | 5.0 |
| Encapsulated Material 2 | 10.0 |

EXAMPLE 5

The composition of Paste AA-2 is reported in Table 4 (each component reported in wt.-%). Paste AA-2 was prepared in bulk. BisGMA and TEGDMA were combined (1:1 by weight) and stirred until homogeneous. The BisGMA/TEGDMA mixture was combined with BPO and CPQ in a mixing cup. The filled cup was placed in a FlackTek SPEEDMIXER and the contents were mixed at 2400 rpm until a homogeneous mixture was achieved. Fumed silica (AEROSIL R972) was added to the cup. The cup was placed in a FlackTeK SPEEDMIXER and the contents were mixed at 2400 rpm until a homogeneous mixture of Paste AA-2 was achieved.

The composition of Paste BB-3 is reported in Table 5 (each component reported in wt.-%). BisGMA and TEGDMA were combined (1:1 by weight) and stirred until homogeneous. The BisGMA/TEGDMA mixture was combined with DMAPE and BHT in a mixing cup. The filled cup was placed in a FlackTek SPEEDMIXER and the contents were mixed at 2400 rpm until a homogeneous mixture was achieved. Fumed silica (AEROSIL R972) was added to the cup. The cup was placed in a FlackTeK SPEEDMIXER and the contents were mixed at 2400 rpm until a homogeneous mixture was achieved. Encapsulated Material 2 was added to the cup. The cup was placed in a FlackTeK SPEED- MIXER and the contents were mixed at 2400 rpm until a homogeneous mixture of Paste BB-2 was achieved.

Pastes AA-2 and BB-3 were combined in a 1:1 volume ratio on a mixing pad at room temperature conditions (about 23° C.) without use of a curing light (dark curing). The resulting sealant composition hardened within 1 minute.

Alternatively, Pastes AA-2 and BB-3 were combined in a 1:1 volume ratio on a mixing pad at room temperature conditions (about 23° C.) and immediately cured using an Elipar™ DeepCure-S LED curing light (3M Oral Care). The resulting sealant composition hardened after exposure to the light for 10 seconds.

TABLE 4

Composition of Paste AA-2

| Component | Weight Percent (wt.-%) in the Composition |
|---|---|
| BisGMA/TEGDMA (1:1 by weight) | 89.92 |
| BPO | 2.81 |
| CPQ | 0.09 |
| Fumed Silica (AEROSIL R972) | 7.18 |

TABLE 5

Composition of Paste BB-3

| Component | Weight Percent (wt.-%) in the Composition |
|---|---|
| BisGMA/TEGDMA (1:1 by weight) | 81.22 |
| DMAPE | 4.13 |
| BHT | 0.09 |
| Fumed Silica (AEROSIL R972) | 4.85 |
| Encapsulated Material 2 | 9.71 |

EXAMPLE 6

A two chamber syringe device with a dispensing nozzle and static mixer as described in FIGS. 1-4 was used. Dimensions of the syringe device were as follows: cartridge length=73.8 mm, cartridge exterior diameter=8.4 mm, volume of each chamber=1 mL, total volume of the dispensing nozzle=0.03 mL, diameter of dispensing nozzle outlet orifice=0.85 mm, nozzle tip length=9 mm., interior included angle of the nozzle tip=120°. A static mixer as described for FIG. 4 was inserted in the cannula portion of the dispensing nozzle. The overall length of the series of mixing paddles was 15 mm. The two chambers each had a substantially D-shaped cross section and the D-shapes were oriented in a mirrored fashion relative to each other.

One chamber of the syringe was partially filled (⅔ by volume) with Paste AA-2. The second chamber was partially filled (⅔ by volume) with Paste BB-3. Upon depressing the plunger, the filled syringe metered a 1:1 volume ratio of Paste AA-2 and Paste BB-3 into the dispensing nozzle. A typodont model of the upper arch of teeth in the human mouth was used with each tooth having deep fissures. The syringe device was used to apply a thin coating of the sealant composition onto the surfaces of 10 teeth in the model. It was observed that upon application the sealant composition penetrated into the fissures. The total time to apply the sealant composition to the ten teeth was about 45 seconds. The sealant composition hardened about 45 seconds after application to a tooth.

EXAMPLE 7

A two chamber syringe device as described in Example 6 was used. One chamber of the syringe was partially filled (⅔ by volume) with Paste AA-1. The second chamber was partially filled (⅔ by volume) with Paste BB-1. Upon depressing the plunger, the filled syringe metered a 1:1 volume ratio of Paste AA-1 and Paste BB-1 into the dispensing nozzle. The syringe device was used to fill a Teflon disk mold (3.1 mm diameter and 1.3 mm height) with the paste. The paste was then cured using an ELIPAR S10 curing light (3M Oral Care) for 20 seconds on each side of the mold. The resulting molded disk was immediately removed from the mold and placed in a 2 mL plastic centrifuge tube that contained 0.5 mL of buffered solution, mixed as 15 g of deionized water and 10 g of a pH 4 buffer solution (Buffer BDH5018, VWR International). The disk was completely submerged in in the buffered solution. The tube was capped and stored at room temperature.

The pH of the buffered solution was measured using an ORION PERPHECT ROSS pH Micro Electrode (catalog number 8220BNWP, Thermo Fisher Scientific Company, Waltham, Pa.). The sample was gently shaken before each measurement. The pH measurements were taken immediately after submersion of the disk in the buffer solution ("0 hr" in Table), and at 15 hours and 39 hours after submersion.

A comparative example molded disk was prepared and tested according to the described procedure with the only change being that Paste BB-1 was replaced with Paste BB-C1 that did not contain any Encapsulated Material 1 (Table 6). The pH profiles are reported in Table 7.

TABLE 6

Composition of Paste BB-C1

| Component | Weight Percent (wt.-%) in the Composition |
|---|---|
| BisGMA/TEGDMA (1:1 by weight) | 92.52 |
| DMAPE | 1.39 |
| BHT | 0.09 |
| Fumed Silica (AEROSIL R972) | 6.0 |
| Encapsulated Material 1 | 0.0 |

EXAMPLE 8

The same procedure and test method as described in Example 7 was followed with the exception that the Encapsulated Material 1 in Paste BB-1 was replaced with an equivalent amount of non-encapsulated Portland cement (wt.-%=10%). to the described procedure with the only change being that Paste BB-1 did not contain any Encapsulated Material 2. The pH profiles are reported in Table 6.

TABLE 7 pH Measurements of PBS Solutions in Contact with Molded Disks Prepared from Examples 7 and 8

| | pH of PBS Solution | | |
|---|---|---|---|
| | 0 hr | 15 hr | 39 hr |
| Example 7 Disk (prepared with Paste BB-1 containing Encapsulated Material 1) | 4.123 | 4.315 | 4.377 |

TABLE 7-continued pH Measurements of PBS Solutions in Contact with
Molded Disks Prepared from Examples 7 and 8

|  | pH of PBS Solution | | |
| --- | --- | --- | --- |
|  | 0 hr | 15 hr | 39 hr |
| Example 8 Disk (prepared with a paste containing Non-Encapsulated Portland Cement) | 4.096 | 4.374 | 4.332 |
| Comparative Example Disk (prepared with Paste BB-C1) | 4.124 | 4.127 | 4.136 |

EXAMPLE 9

The composition of Paste BB-4 is reported in Table 8 (each component reported in wt.-%). BisGMA and TEGDMA can be combined (1:1 by weight) with stirring until homogeneous. The BisGMA/TEGDMA mixture is combined with DMAPE and BHT in a mixing cup. The filled cup is placed in a FlackTek SPEEDMIXER and the contents are mixed at about 2400 rpm until a homogeneous mixture is achieved. Fumed silica (AEROSIL R972) is added to the cup. The cup is placed in a FlackTeK SPEEDMIXER and the contents are mixed at about 2400 rpm until a homogeneous mixture is achieved. Encapsulated Material 1 is added to the cup. The cup is placed in a FlackTeK SPEEDMIXER and the contents are mixed at about 2400 rpm until a homogeneous mixture of Paste BB-4 is achieved.

Pastes AA-1 and BB-4 are combined in an approximately 1:1 volume ratio on a mixing pad to provide the resulting sealant composition.

EXAMPLE 10

The composition of Paste BB-5 is reported in Table 8 (each component reported in wt.-%). BisGMA and TEGDMA can be combined (1:1 by weight) with stirring until homogeneous. The BisGMA/TEGDMA mixture is combined with DMAPE and BHT in a mixing cup. The filled cup is placed in a FlackTek SPEEDMIXER and the contents are mixed at about 2400 rpm until a homogeneous mixture is achieved. Fumed silica (AEROSIL R972) is added to the cup. The cup is placed in a FlackTeK SPEEDMIXER and the contents are mixed at about 2400 rpm until a homogeneous mixture is achieved. Encapsulated Material 1 is added to the cup. The cup is placed in a FlackTeK SPEEDMIXER and the contents are mixed at about 2400 rpm until a homogeneous mixture of Paste BB-5 is achieved.

Pastes AA-1 and BB-5 are combined in an approximately 1:1 volume ratio on a mixing pad to provide the resulting sealant composition.

EXAMPLE 11

The composition of Paste BB-6 is reported in Table 8 (each component reported in wt.-%). BisGMA and TEGDMA can be combined (1:1 by weight) with stirring until homogeneous. The BisGMA/TEGDMA mixture is combined with DMAPE and BHT in a mixing cup. The filled cup is placed in a FlackTek SPEEDMIXER and the contents are mixed at about 2400 rpm until a homogeneous mixture is achieved. Fumed silica (AEROSIL R972) is added to the cup. The cup is placed in a FlackTeK SPEEDMIXER and the contents are mixed at about 2400 rpm until a homogeneous mixture is achieved. Encapsulated Material 1 is added to the cup. The cup is placed in a FlackTeK SPEEDMIXER and the contents are mixed at about 2400 rpm until a homogeneous mixture of Paste BB-6 is achieved.

Pastes AA-1 and BB-6 are combined in an approximately 1:1 volume ratio on a mixing pad to provide the resulting sealant composition.

EXAMPLE 12

The composition of Paste BB-7 is reported in Table 8 (each component reported in wt.-%). BisGMA and TEGDMA can be combined (1:1 by weight) with stirring until homogeneous. The BisGMA/TEGDMA mixture is combined with DMAPE and BHT in a mixing cup. The filled cup is placed in a FlackTek SPEEDMIXER and the contents are mixed at about 2400 rpm until a homogeneous mixture is achieved. Fumed silica (AEROSIL R972) is added to the cup. The cup is placed in a FlackTeK SPEEDMIXER and the contents are mixed at about 2400 rpm until a homogeneous mixture is achieved. Encapsulated Material 1 is added to the cup. The cup is placed in a FlackTeK SPEEDMIXER and the contents are mixed at about 2400 rpm until a homogeneous mixture of Paste BB-7 is achieved.

Pastes AA-1 and BB-7 are combined in an approximately 1:1 volume ratio on a mixing pad to provide the resulting sealant composition.

EXAMPLE 13

The composition of Paste BB-8 is reported in Table 8 (each component reported in wt.-%). BisGMA and TEGDMA can be combined (1:1 by weight) with stirring until homogeneous. The BisGMA/TEGDMA mixture is combined with DMAPE and BHT in a mixing cup. The filled cup is placed in a FlackTek SPEEDMIXER and the contents are mixed at about 2400 rpm until a homogeneous mixture is achieved. Fumed silica (AEROSIL R972) is added to the cup. The cup is placed in a FlackTeK SPEEDMIXER and the contents are mixed at about 2400 rpm until a homogeneous mixture is achieved. Encapsulated Material 1 is added to the cup. The cup is placed in a FlackTeK SPEEDMIXER and the contents are mixed at about 2400 rpm until a homogeneous mixture of Paste BB-8 is achieved.

Pastes AA-1 and BB-8 are combined in an approximately 1:1 volume ratio on a mixing pad to provide the resulting sealant composition.

EXAMPLE 14

The composition of Paste BB-9 is reported in Table 8 (each component reported in wt.-%). BisGMA and TEGDMA can be combined (1:1 by weight) with stirring until homogeneous. The BisGMA/TEGDMA mixture is combined with DMAPE and BHT in a mixing cup. The filled cup is placed in a FlackTek SPEEDMIXER and the contents are mixed at about 2400 rpm until a homogeneous mixture is achieved. Fumed silica (AEROSIL R972) is added to the cup. The cup is placed in a FlackTeK SPEEDMIXER and the contents are mixed at about 2400 rpm until a homogeneous mixture is achieved. Encapsulated Material 1 is added to the cup. The cup is placed in a FlackTeK SPEEDMIXER and the contents are mixed at about 2400 rpm until a homogeneous mixture of Paste BB-9 is achieved.

Pastes AA-1 and BB-9 are combined in an approximately 1:1 volume ratio on a mixing pad to provide the resulting sealant composition.

TABLE 8

Compositions of Pastes BB-4, BB-5, BB-6, BB-7, BB-8, and BB-9

| Component | Weight Percent (wt.-%) in the Composition (Pastes BB-4 to BB-9) | | | | | |
|---|---|---|---|---|---|---|
| | BB-4 | BB-5 | BB-6 | BB-7 | BB-8 | BB-9 |
| BisGMA/TEGDMA (1:1 by weight) | 86.55 | 81.74 | 76.93 | 72.12 | 67.31 | 62.51 |
| DMAPE | 1.30 | 1.23 | 1.15 | 1.08 | 1.01 | 0.94 |
| BHT | 0.09 | 0.08 | 0.08 | 0.07 | 0.07 | 0.06 |
| Fumed Silica (AEROSIL R972) | 2.06 | 1.95 | 1.84 | 1.73 | 1.61 | 1.49 |
| Encapsulated Material 1 | 10.0 | 15.0 | 20.0 | 25.0 | 30.0 | 35.0 |

What is claimed is:

1. A two-part dental sealant composition comprising:
 a first part comprising a (meth)acrylate resin and an oxidizing curing agent,
  the first part characterized by a viscosity of no greater than 5000 cps;
 a second part comprising a (meth)acrylate resin and a reducing curing agent,
  the second part characterized by a viscosity of no greater than 5000 cps; and
 an encapsulated material comprising:
  a core comprising:
   a basic material or a basic compound characterized by a pKa of 8-14, and
   a source of calcium ions derived from the basic material or the basic compound, a calcium compound other than the basic material or the basic compound, or a combination thereof; and
  a shell comprising a metal oxide,
 wherein the shell surrounds the core, and
 wherein the shell degrades, dissolves, or decomposes upon contact with water or an acidic component.

2. The two-part dental sealant composition of claim 1, wherein one or more of:
 the oxidizing curing agent is a peroxide; and
 the reducing curing agent is an amine.

3. The two-part dental sealant composition of claim 1, wherein the (meth)acrylate resin of the first part and the (meth)acrylate resin of the second part each comprise bisphenol A glycidyl methacrylate and triethylene glycol dimethacrylate.

4. The two-part dental sealant composition of claim 1, the core further comprising a source of phosphorus ions, fluoride ions, or a combination thereof.

5. The two-part dental sealant composition of claim 1, the core comprising tricalcium silicate, dicalcium silicate, calcium silicate, tricalcium aluminate, tetracalcium aluminoferrite, or a combination thereof.

6. The two-part dental sealant composition of claim 1, the core further comprising magnesium oxide, calcium oxide, potassium sulfate, sodium sulfate, or a combination thereof.

7. The two-part dental sealant composition of claim 1, the core comprising a bioactive glass.

8. The two-part dental sealant composition of claim 1, wherein the basic material or the basic compound is present in an amount of at least 25 wt % based on the weight of the core.

9. The two-part dental sealant composition of claim 1, wherein the shell has a thickness of up to 500 nm.

10. The two-part dental sealant composition of claim 1, further comprising a photoinitiator.

11. A kit for storing and applying a dental sealant comprising:
 i) a syringe device comprising:
  a) a cartridge including a first chamber and a second chamber,
  b) a plunger comprising a first rod and a second rod, wherein the first rod seals the first chamber and the second rod seals the second chamber, and
  c) at least one dispensing nozzle comprising a static mixer and an outlet,
   wherein the at least one dispensing nozzle is attached to an end of the cartridge that is opposite the plunger; and
 ii) a two-part dental sealant composition of claim 1,
  wherein the first part is located in the first chamber, and
  wherein the second part is located in the second chamber.

12. The kit of claim 11, the cartridge characterized by a volume no greater than 5 cc.

13. The kit of claim 11, the first chamber and second chamber having a volume ratio of about 1:1.

14. The kit of claim 11, the dispensing nozzle characterized by a volume no greater than 0.25 cc.

15. The kit of claim 11, the outlet characterized by a diameter of no greater than 1.5 mm.

16. A method of applying a two-part dental sealant comprising:
 providing a kit of claim 11; and
 applying pressure to the plunger thereby conveying the first part and the second part of the two-part dental sealant through the static mixer and the outlet onto a tooth surface.

17. The method of claim 16, wherein the two-part dental sealant composition cures when the first part and the second part are combined without exposure to actinic radiation.

18. The method of claim 16, wherein the two-part dental sealant composition cures when the first part and the second part combined within 5 minutes.

19. The method of claim 16, further comprising conditioning the tooth surface, wherein the conditioning is performed prior to applying the dental sealant.

20. The method of claim 19, wherein the conditioning comprises etching, priming, abrading, or a combination thereof.

* * * * *